United States Patent
Ban et al.

(10) Patent No.: US 10,283,088 B2
(45) Date of Patent: May 7, 2019

(54) METHOD AND APPARATUS FOR PROVIDING MEDICAL INFORMATION

(71) Applicant: SAMSUNG ELECTRONICS CO., LTD., Suwon-si (KR)

(72) Inventors: Dae-hyun Ban, Seoul (KR); Woong Lee, Suwon-si (KR); Jeong-ho Han, Seoul (KR); Keum-yong Oh, Yongin-si (KR); Chang-lae Lee, Hadong-gun (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 285 days.

(21) Appl. No.: 14/303,086

(22) Filed: Jun. 12, 2014

(65) Prior Publication Data
US 2014/0368545 A1    Dec. 18, 2014

(30) Foreign Application Priority Data

Jun. 12, 2013  (KR) .................. 10-2013-0067304
Jun. 11, 2014  (KR) .................. 10-2014-0071055

(51) Int. Cl.
*A61B 6/00* (2006.01)
*A61B 6/03* (2006.01)
(Continued)

(52) U.S. Cl.
CPC ........... *G09G 5/14* (2013.01); *A61B 6/03* (2013.01); *A61B 6/463* (2013.01); *G01R 33/283* (2013.01); *G01R 33/546* (2013.01); *G06F 3/1423* (2013.01); *G06F 19/00* (2013.01); *G06T 7/0012* (2013.01); *G16H 40/63* (2018.01); *A61B 6/032* (2013.01); *G06T 2207/10072* (2013.01); *G06T 2207/30004* (2013.01); *G09G 2340/12* (2013.01)

(58) Field of Classification Search
None
See application file for complete search history.

(56) References Cited

U.S. PATENT DOCUMENTS 6,302,579 B1 * 10/2001 Meyer .................. A61B 6/4429
                                                                378/195
7,343,189 B2    3/2008 Kagermeier
(Continued)

FOREIGN PATENT DOCUMENTS

CN       100358473 C     1/2008
CN       100483433 C     4/2009
(Continued)

OTHER PUBLICATIONS

Philips Allura "Advanced intervention in your lab" Koninldijke Philips Electronics N.V. Nov. 2010.*
(Continued)

*Primary Examiner* — Aaron M Richer
*Assistant Examiner* — Khoa Vu
(74) *Attorney, Agent, or Firm* — Sughrue Mion, PLLC

(57) ABSTRACT

The medical information providing method includes: capturing a room image of an inside of an examination room in which an object is positioned for medical examination; obtaining diagnostic information of the object; and displaying the diagnostic information which is overlaid on the room image according to a first mode, on a display.

50 Claims, 26 Drawing Sheets

(51) Int. Cl.
*G06F 3/14* (2006.01)
*G06T 7/00* (2017.01)
*G09G 5/14* (2006.01)
*G01R 33/28* (2006.01)
*G01R 33/54* (2006.01)
*G06F 19/00* (2018.01)
*G16H 40/63* (2018.01)

(56) References Cited

U.S. PATENT DOCUMENTS

| | | | |
|---|---|---|---|
| 8,338,786 B2 | 12/2012 | Albrecht | |
| 8,338,810 B2 | 12/2012 | Hoernig | |
| 2002/0118280 A1 | 8/2002 | Medlar et al. | |
| 2005/0020911 A1 | 1/2005 | Viswanathan et al. | |
| 2005/0107681 A1* | 5/2005 | Griffiths | A61B 5/0046 600/410 |
| 2005/0203389 A1 | 9/2005 | Williams | |
| 2005/0254505 A1 | 11/2005 | Chang et al. | |
| 2006/0100497 A1* | 5/2006 | Sawazaki | A61B 5/0002 600/407 |
| 2006/0261296 A1* | 11/2006 | Heath | A61B 6/4494 250/580 |
| 2007/0050828 A1* | 3/2007 | Renzi | H04N 7/141 725/93 |
| 2007/0253531 A1* | 11/2007 | Okuzawa | A61B 6/00 378/62 |
| 2008/0217564 A1 | 9/2008 | Beyar et al. | |
| 2010/0053213 A1 | 3/2010 | Ishida et al. | |
| 2010/0059679 A1 | 3/2010 | Albrecht | |
| 2010/0189322 A1* | 7/2010 | Sakagawa | G06F 19/321 382/128 |
| 2011/0037840 A1* | 2/2011 | Hiltl | 348/61 |
| 2011/0075813 A1* | 3/2011 | Venturino | A61B 6/4283 378/98.8 |
| 2012/0051520 A1* | 3/2012 | Hoernig | A61B 6/107 378/98.5 |
| 2012/0256886 A1* | 10/2012 | Ryu | G06F 1/1632 345/204 |
| 2012/0320093 A1* | 12/2012 | Zhu | G06F 19/3406 345/634 |
| 2013/0006094 A1* | 1/2013 | Charles | A61B 5/055 600/411 |
| 2013/0094628 A1* | 4/2013 | Lalena | A61B 6/4283 378/98 |
| 2014/0155728 A1 | 6/2014 | Lee et al. | |
| 2014/0275970 A1* | 9/2014 | Brown | G01R 33/3692 600/413 |

FOREIGN PATENT DOCUMENTS

| | | |
|---|---|---|
| CN | 101664310 A | 3/2010 |
| CN | 102379717 A | 3/2012 |
| CN | 103845071 A | 6/2014 |
| JP | 9-33856 A | 2/1997 |
| JP | 2003-265460 A | 9/2003 |
| JP | 2004-180834 A | 7/2004 |
| JP | 2004180834 A | 7/2004 |
| JP | 2010057528 A | 3/2010 |
| JP | 2012115299 A | 6/2012 |
| KR | 1020040077609 A | 9/2004 |

OTHER PUBLICATIONS

Philips Allura "Advanced interventions in your lab" 2010 Koninldijke Philips Electronics.*
"Advanced intervention in your lab" Nov. 2010 Koninldijke Philips Electronics N.V. (Year: 2010).*
Communication dated Sep. 23, 2014, issued by the International Searching Authority in counterpart International Application No. PCT/KR2014/005175.
Communication dated Jul. 24, 2015 by the European Patent Office in related Application No. 14172191.0.
Communication dated Oct. 7, 2015 by the Korean Intellectual Patent Office in related Application No. 10-2014-0071055.
Communication dated Jan. 29, 2018, from the State Intellectual Property Office of People's Republic of China in counterpart Application No. 201480045372.4.

* cited by examiner

FIG. 18
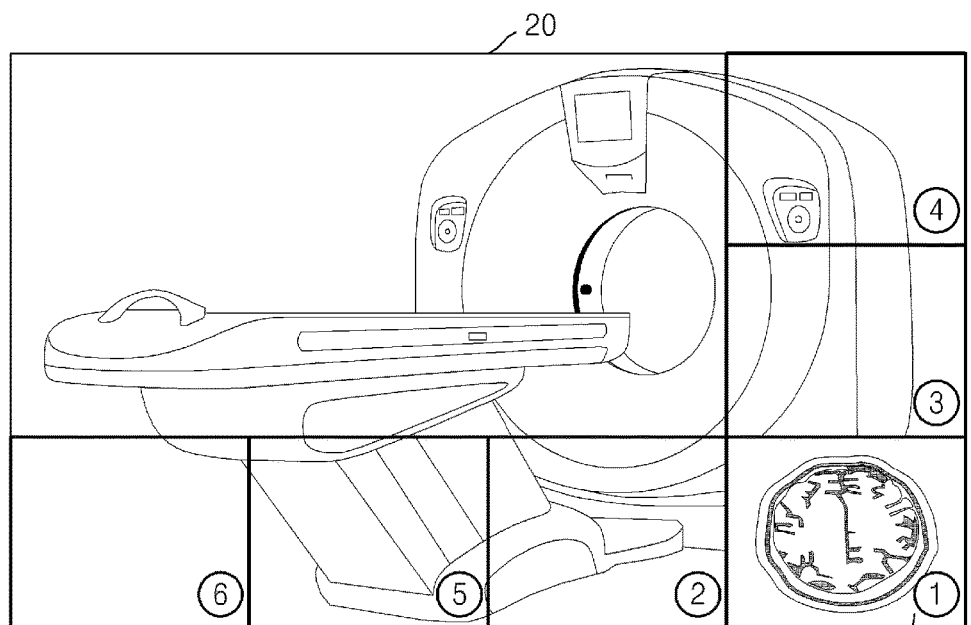
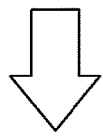
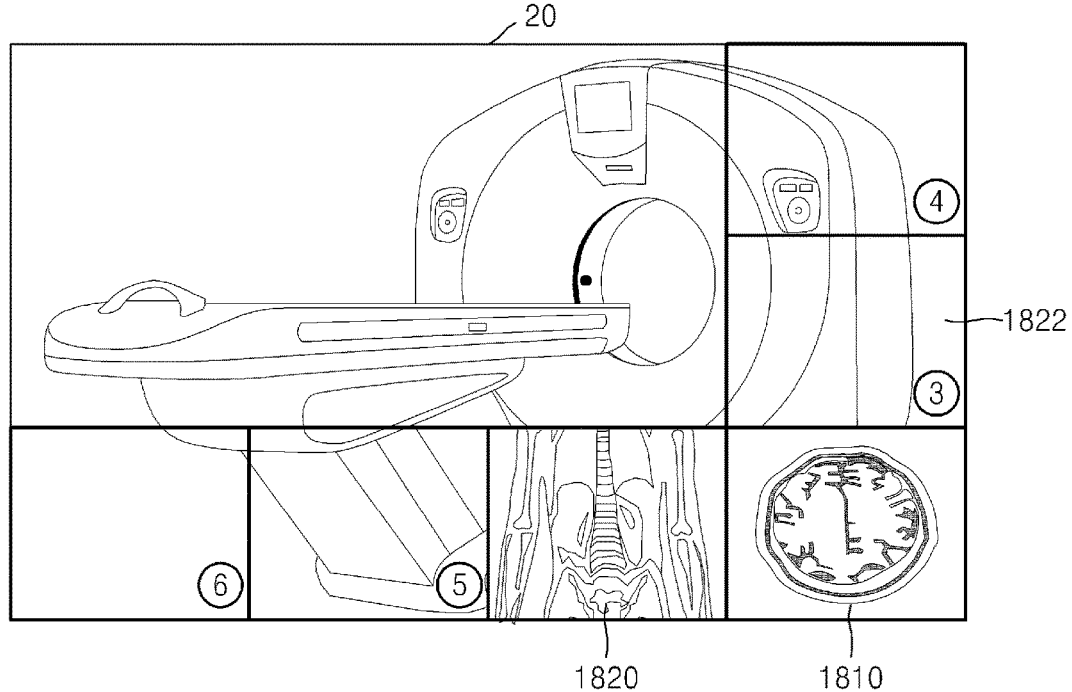

FIG. 19
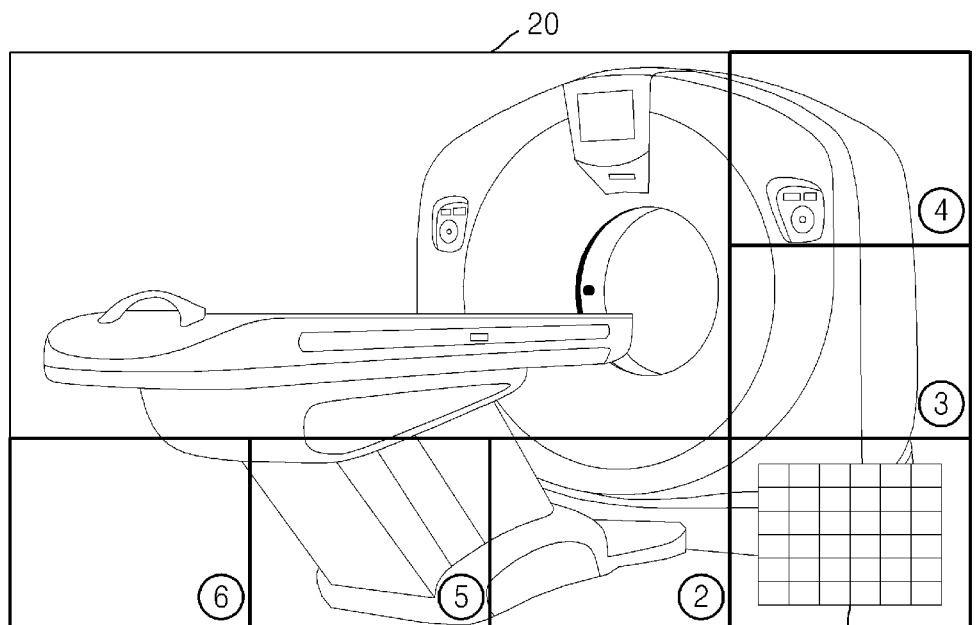
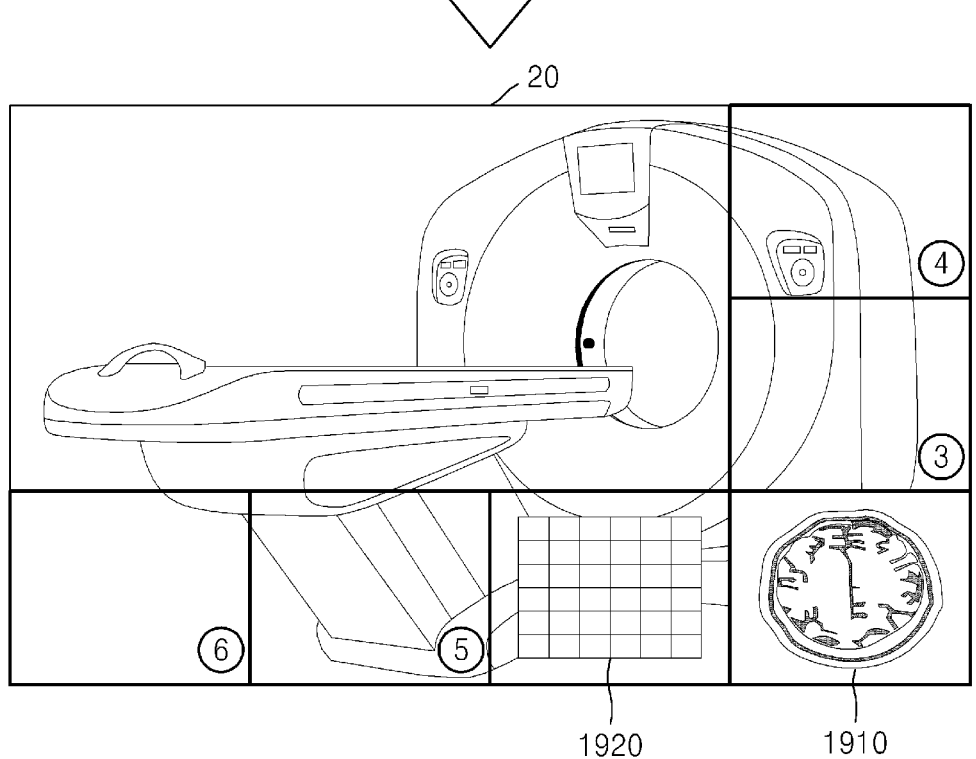

METHOD AND APPARATUS FOR PROVIDING MEDICAL INFORMATION

CROSS-REFERENCE TO RELATED PATENT APPLICATIONS

This application claims priority from Korean Patent Application No. 10-2013-0067304, filed on Jun. 12, 2013, and Korean Patent Application No. 10-2014-0071055, filed on Jun. 11, 2014, in the Korean Intellectual Property Office, the disclosure of which is incorporated herein in its entirety by reference.

BACKGROUND

1. Field

Apparatuses and methods consistent with exemplary embodiments relate to providing medical information, from a medical information providing apparatus to a user.

2. Description of the Related Art

A computed tomography (CT) system captures a plurality of X-ray images while the CT system rotates around one or more axes with respect to an object, and then synthesizes the plurality of X-ray images. Since the CT system is capable of providing a cross-sectional image of the object, the CT system may express an inner structure of the object without an overlap therebetween, compared to a general X-ray capturing apparatus, so that the CT system is widely used.

A magnetic resonance imaging (MRI) system involves imaging information that is obtained by exposing nuclei to a magnetic field and then resonating the nuclei. The MRI apparatus is advantageous in that it is noninvasive, exhibits an excellent tissue contrast, compared to a CT apparatus, and does not generate artifacts due to bone tissue. Also, since the MRI apparatus can capture various cross-sectional images in predetermined directions without moving an object, the MRI apparatus may be widely used with other image diagnostic apparatuses.

In regard to a CT or an MRI system, a console room in which an operator or a user is positioned is shielded from an examination room in which an object is positioned for imaging. A plurality of display devices and user interface devices are positioned in the console room to diagnose the object.

It may be difficult for the operator to efficiently use a space in the console room and may be cumbersome to operate a plurality of display devices and user interface devices, which may result in the increased costs and decreased throughput of the medical system. Also, if an operator's focus is disrupted, the medical examination may be inaccurately performed.

In detail, if an operator's view of the object through the window is obscured (for example by the presence of a monitor, other display device or paperwork on the operator's desk) or if the operator's attention is drawn to diagnostic information shown on one or more display devices in front of or near the operator, there is a risk that the operator's observation of the object in the shield room through the window of the console room may become careless.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

One or more exemplary embodiments provide a medical information providing method and apparatus therefor that efficiently provide medical information by efficiently disposing a plurality of display devices.

One or more embodiments also provide a non-transitory computer-readable recording medium having recorded thereon a program which, when executed by a computer, performs the medical information providing method.

According to an aspect of an exemplary embodiment, a medical information providing method includes operations of capturing a shield room inside image of a shield room in which an object is positioned; obtaining diagnostic information related to the object; determining a medical information providing mode as one of a first mode for providing the shield room inside image, a second mode for providing the diagnostic information, and a third mode for providing the shield room inside image and the diagnostic information; and providing at least one of the shield room inside image and the diagnostic information to a display, according to the medical information providing mode, wherein the display is disposed adjacent to a console room window for observation of the shield room.

The medical information providing method may further include an operation of selecting a partial region of the shield room inside image, and an image of the partial region may be provided to the display.

The operation of selecting may include an operation of selecting the partial region based on at least one of a position of the display, a position of an operator, and a distance between the display and the operator.

The operation of selecting may include an operation of selecting the partial region based on at least one identification (ID) device for identifying the operator.

The operation of selecting may include an operation of selecting the partial region based on the at least one ID device of the operator that logs into a medical diagnostic system for diagnosing the object.

The operation of determining may include an operation of determining the medical information providing mode while a diagnostic process with respect to the object is being performed.

The operation of determining may include an operation of changing the first mode to the second mode or the third mode, when the diagnostic process with respect to the object starts.

When a plurality of the displays exists, the operation of determining may include an operation of determining the medical information providing mode of each of the plurality of the displays.

When a number of pieces of obtained diagnostic information are increased, the operation of determining may include an operation of determining the medical information providing mode of each of the plurality of the displays as the second mode or the third mode.

The operation of determining may include an operation of changing the medical information providing mode of each of the plurality of the displays, according to priority orders that are pre-set in the plurality of the displays.

The priority orders may be determined based on at least one of a position, a size, and a resolution of each of the plurality of the displays.

When a number of pieces of obtained diagnostic information are increased, the providing may include an operation of providing medical information, which has been provided to a first display, to a second display that is lower, in terms of the priority orders, than the first display.

The plurality of the displays may be disposed adjacent to each other along a side edge of the console room window.

The medical information providing method may further include operations of selecting a plurality of partial regions from the shield room inside image according to an arrangement of the plurality of the displays; and matching the plurality of partial regions with the plurality of the displays, respectively, and images of the plurality of partial regions may be provided to the plurality of the matched displays.

The plurality of partial regions may be spatially connected to each other.

The medical information providing method may further include operations of receiving an external input signal via a user input unit that commonly corresponds to the plurality of the displays; and controlling the plurality of the displays based on the external input signal.

In the third mode, the diagnostic information may be overlaid on the shield room inside image.

The diagnostic information may include at least one of ID information of the object, information about a diagnostic process with respect to the object, and diagnostic history information of the object.

A medical diagnostic system for diagnosing the object may include an MRI system or a CT system.

According to an aspect of an exemplary embodiment, a medical information providing apparatus includes an image obtainer for capturing a shield room inside image of a shield room in which an object is positioned; a diagnostic information obtainer for obtaining diagnostic information related to the object; a mode determiner for determining a medical information providing mode as one of a first mode for providing the shield room inside image, a second mode for providing the diagnostic information, and a third mode for providing the shield room inside image and the diagnostic information; and a controller for providing at least one of the shield room inside image and the diagnostic information to a display, according to the medical information providing mode, wherein the display is disposed adjacent to a console room window for observation of the shield room.

According to an aspect of an exemplary embodiment, there is provided a non-transitory computer-readable recording medium having recorded thereon a program which, when executed by a computer, performs the method.

According to one or more exemplary embodiments, a medical information providing apparatus includes the display unit disposed adjacent or next to, or in or on the console room window for enlarging an observation area inside the shield room, when the shield room inside image is provided to the display unit in at least the first mode, relative to an observation area that the console room window provides when the shield room inside view is not provided to the display unit in the second mode.

According to one or more exemplary embodiments of the present disclosure, a medical information providing method is provided to include the display unit disposed adjacent or next to, or in or on the console room window for enlarging an observation area inside the shield room when the shield room inside image is provided to the display unit, wherein the enlarged observation area is larger than an observation area that the console room window provides.

BRIEF DESCRIPTION OF THE DRAWINGS

The above and/or other aspects will become more apparent by describing certain exemplary embodiments, with reference to the accompanying drawings, in which:

FIG. 18 illustrates an example in which the medical information providing apparatus outputs diagnostic information according to priority orders of displays, according to an exemplary embodiment;

FIG. 19 illustrates an example in which the medical information providing apparatus outputs diagnostic information to displays according to importance of the diagnostic information, according to an exemplary embodiment;

DETAILED DESCRIPTION

Figure 1:
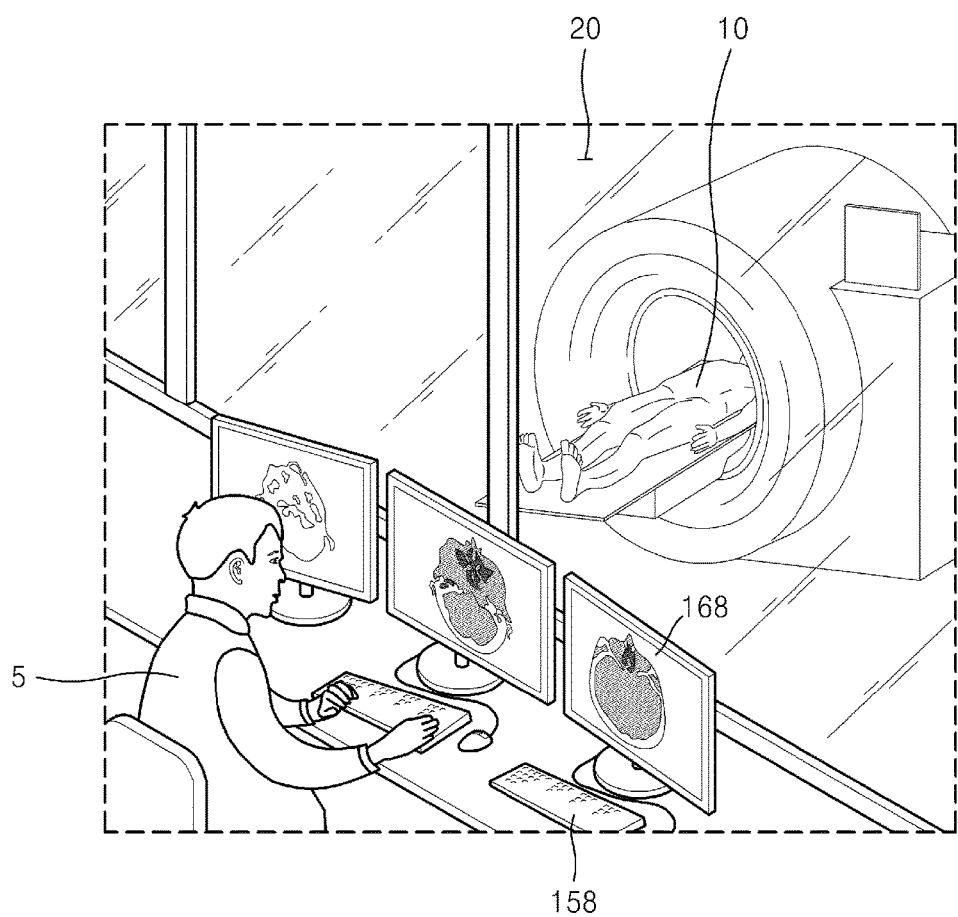
FIG. 1 illustrates a concept related to exemplary embodiments.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

All terms including descriptive or technical terms which are used herein should be construed as having meanings that are obvious to one of ordinary skill in the art. However, the terms may have different meanings according to an intention of one of ordinary skill in the art, precedent cases, or the appearance of new technologies. Also, some terms may be arbitrarily selected by the applicant, and in this case, the meaning of the selected terms will be described in detail in the detailed description of the invention. Thus, the terms used herein have to be defined based on the meaning of the terms together with the description throughout the specification.

Also, when a part "includes" or "comprises" an element, unless there is a particular description contrary thereto, the part may further include other elements, not excluding the other elements. In the following description, terms such as "unit" may be embodied as, but not limited to, software or a hardware component, such as a field programmable gate array (FPGA) or application specific integrated circuit (ASIC). However, a unit may advantageously be configured to reside on an addressable storage medium and configured to execute on one or more processors. Thus, a unit may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for in the components and units may be combined into fewer components and units or further separated into additional components and units.

Throughout the specification, an "image" may mean multi-dimensional data formed of discrete image elements (e.g., pixels of a two-dimensional (2D) image and voxels of a three-dimensional (3D) image). For example, the image may include a medical image of an object which is obtained by using an X-ray, CT scanner, MRI, an ultrasonic wave, or other medical diagnostic systems.

Also, throughout the specification, a "target object" may include a human, an animal, or a part of a human or animal. For example, the object may include organs such as liver, heart, womb, brain, breast, abdomen, or the like, or a blood vessel. Also, the object may include a phantom. The phantom means a material having a volume that is very close to a density and effective atomic number of an organism, and may include a sphere phantom having a characteristic similar to a physical body.

Throughout the specification, a "user" may be, but is not limited to, a medical expert including a doctor, a nurse, a medical laboratory technologist, a medial image expert, a radiologist, and a technician who repairs a medical apparatus.

Expressions such as "at least one of," when preceding a list of elements, modify the entire list of elements and do not modify the individual elements of the list.

FIG. 1 illustrates a concept related to exemplary embodiments.

In a medical diagnostic system such as an MRI system, a CT system, an X-ray system, or the like, an operator 5 in a console room images an object 10 disposed in a shield room. The console room and the shield room are separated from each other by a shield wall to protect the operator 5 from a magnetic field, radiation, a radio frequency (RF) signal, or the like.

The operator 5 of the medical diagnostic system may desire to directly observe the inside of the shield room and the object 10 while imaging the object 10. In detail, the console room window 20 is a unit that is used by the operator 5 in the console room to observe the object 10 in shield room. The operator 5 may diagnose the object 10 using presented information that is displayed on monitors, user interfaces or other display devices in front of or near to the operator 5. That is, the operator 5 may desire to directly check various factors such as a position of the object 10 on a diagnostic table, movement of the object 10 during diagnostic imaging, or the like by using a console room window 20.

The operator 5 may image the object 10 while the operator 5 directly observes the object 10 via the console room window 20 that is transparent or translucent.

As illustrated in FIG. 1, the operator 5 may use a plurality of user interfaces 158 and displays 168 to perform medical examination of the object 10. The operator 5 may diagnose the object 10 by controlling a diagnostic process and obtaining a medical image via a plurality of input units and output units of the medical diagnostic system.

Figure 2:
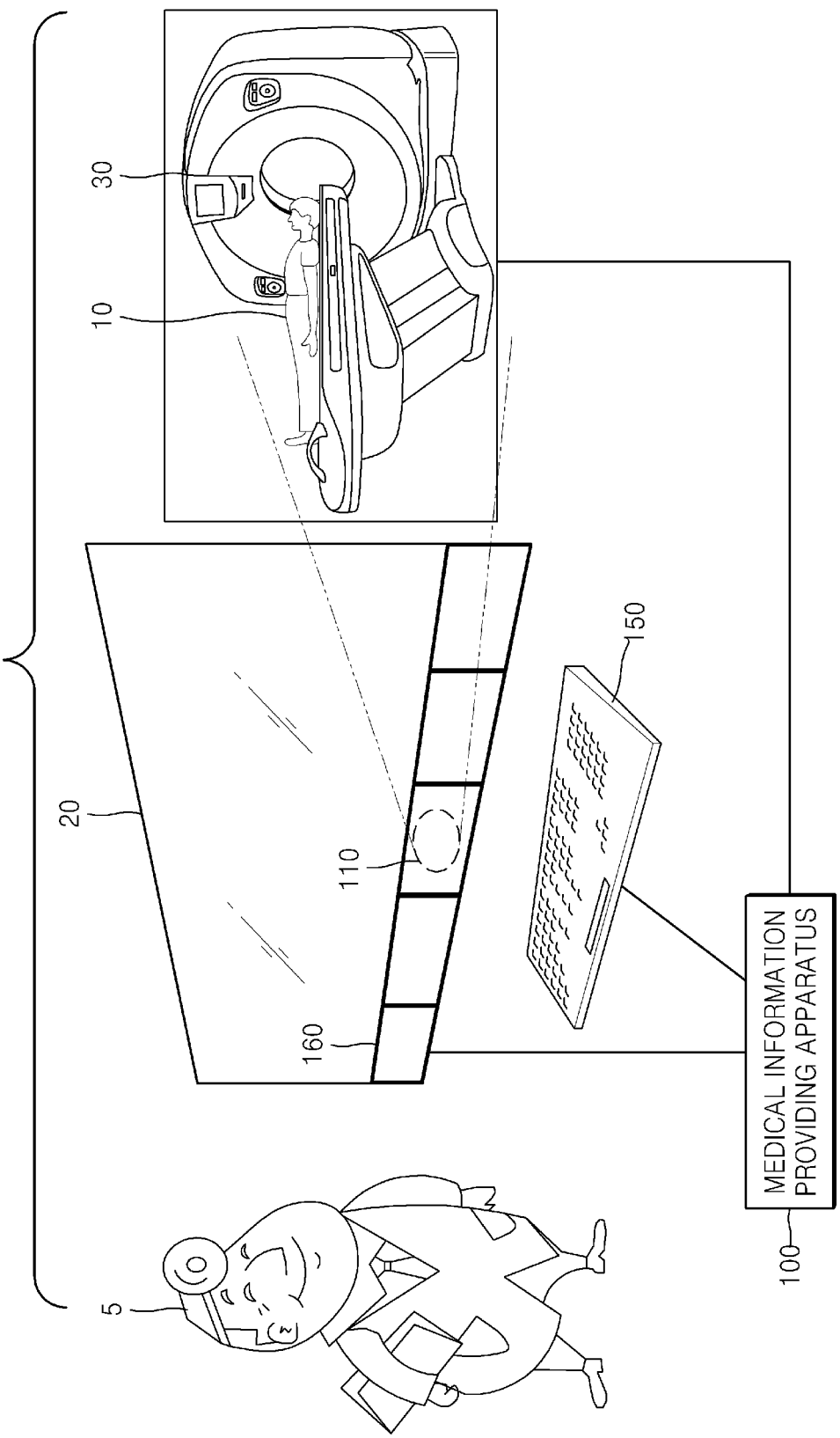
FIG. 2 illustrates a relation between a medical information providing apparatus, a console room window, and a medical diagnostic system, according to an exemplary embodiment.

FIG. 2 illustrates a relation between a medical information providing apparatus 100, the console room window 20, and a medical diagnostic system 30, according to an exemplary embodiment.

As described above with reference to FIG. 1, the operator 5 of the medical information providing apparatus 100 in the console room may observe the object 10 in the shield room, i.e., the examination room, and may also observe operation of the medical diagnostic system 30 via the console room window 20.

The medical information providing apparatus 100 shown in FIG. 2 may be connected to the medical diagnostic system 30, so that the medical information providing apparatus 100 may receive diagnostic information and may display the diagnostic information via one or more displays 160. In the present exemplary embodiment, the medical information providing apparatus 100 may include one or more image obtainers 110 for capturing an image of the inside of a shield room, and may display the shield room inside image via the display 160. Additionally or alternatively, at least one image obtainer 110, such as a camera, may be disposed within the shield room and separate from the displays 160. Thus, a view of the inside of the shield room offered to the operator 5 is enlarged relative to a size of the window 20 defined by a boundary of the window, when the displays 160 are arranged next to or outside the physical boundary of the window 20 and operate in the first mode to show the shield room inside image, or in the third mode with a transparent second mode with shield room inside image of the first mode in the background on the display unit. However, such a camera inside the shield room may need to be protected against influence from a magnetic field, radiation, a radio frequency (RF) signal, or the like.

The medical information providing apparatus 100 may provide, to the operator 5, at least one of the shield room inside image and the diagnostic information via the display 160. An exemplary embodiment in which the medical information providing apparatus 100 provides medical information, i.e., the shield room inside image and the diagnostic information, to the operator 5 is described in detail below.

The diagnostic information may indicate information to be used in diagnosing the object 10, and may include various types of information that are related to the object 10 and that are obtained via the medical diagnostic system 30. For example, the diagnostic information may include pre-stored information that is related to the object 10 and that includes identification (ID) information such as a patient's hospital ID to identify the object 10, patient information such as an age, a name, a gender, or the like of the object 10, information about a medical image capturing history of the object 10, a patient list indicating a medical image capturing schedule, or the like.

In addition, the diagnostic information may also include information about a movement path of a diagnostic table on which the object 10 is positioned, a medical image that is a result of diagnosing the object 10, an image of a path along which a contrast medium that is injected into the object 10 spreads, and information about a progress of a protocol that diagnoses the object 10. However, the diagnostic information is not limited to the aforementioned information but may include all types of information related to the medical examination of the object 10.

The operator 5 of the medical information providing apparatus 100 may observe the inside of the shield room via the console room window 20 and may receive the medical information from the medical information providing apparatus 100. That is, due to the display 160 that is disposed around the console room window 20, the operator 5 may observe and may simultaneously image the object 10 without disruption of his/her view.

A number of the image obtainers 110 and the displays 160, and their positions at the console room window 20 shown in FIG. 2 are not limited to those described above. An exemplary embodiment about the positions of the image obtainers 110 and the displays 160 is described below with reference to FIGS. 12 through 21.

FIG. 3 illustrates a medical information providing mode of the display 160, according to an exemplary embodiment.

The medical information providing apparatus 100 may determine a medical information providing mode of the display 160 to provide medical information. Here, the medical information providing mode means a type of medical information that is output by the medical information providing apparatus 100 via the display 160. The medical information providing apparatus 100 may output the medical information including at least one of a shield room inside image and the diagnostic information, and the medical information providing mode may vary according to a type of the medical information.

For example, a first mode may indicate a case in which the medical information providing apparatus 100 provides the room inside image to the display 160, a second mode may indicate a case in which the medical information providing apparatus 100 provides the diagnostic information, which is obtained from the medical diagnostic system 30, via the display 160, and a third mode may indicate a case in which the medical information providing apparatus 100 provides both the room inside image and the diagnostic information. Hereinafter, the respective first, second, and third modes of the medical information providing mode are described in detail.

The medical information providing apparatus 100 includes a plurality of the displays 160 that are disposed adjacent to the console room window 20. The displays 160 are shown with a dotted line in FIG. 3. An arrangement and positions of the displays 160 are not limited to FIG. 3.

Figure 3A:
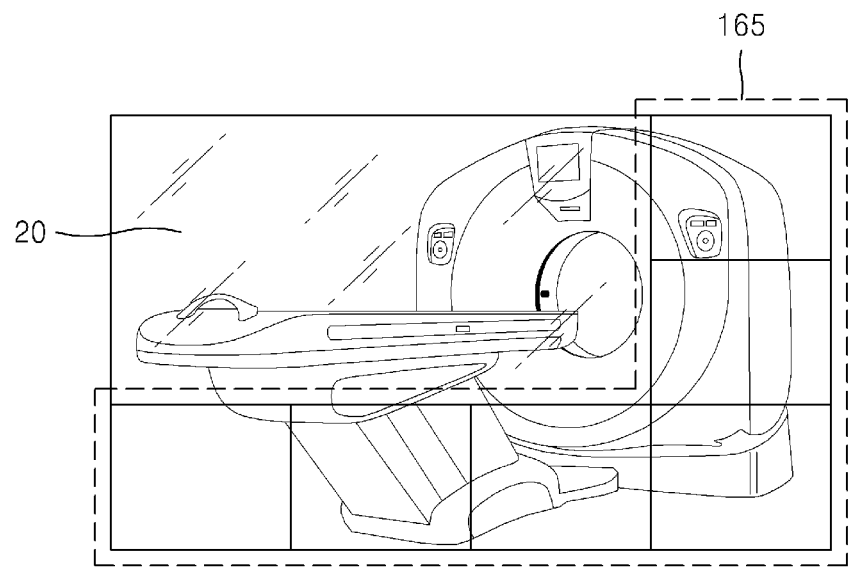
FIGS. 3A, 3B, 3C, and 3D illustrate medical information providing modes of a display, according to an exemplary embodiment.
Figure 3B:
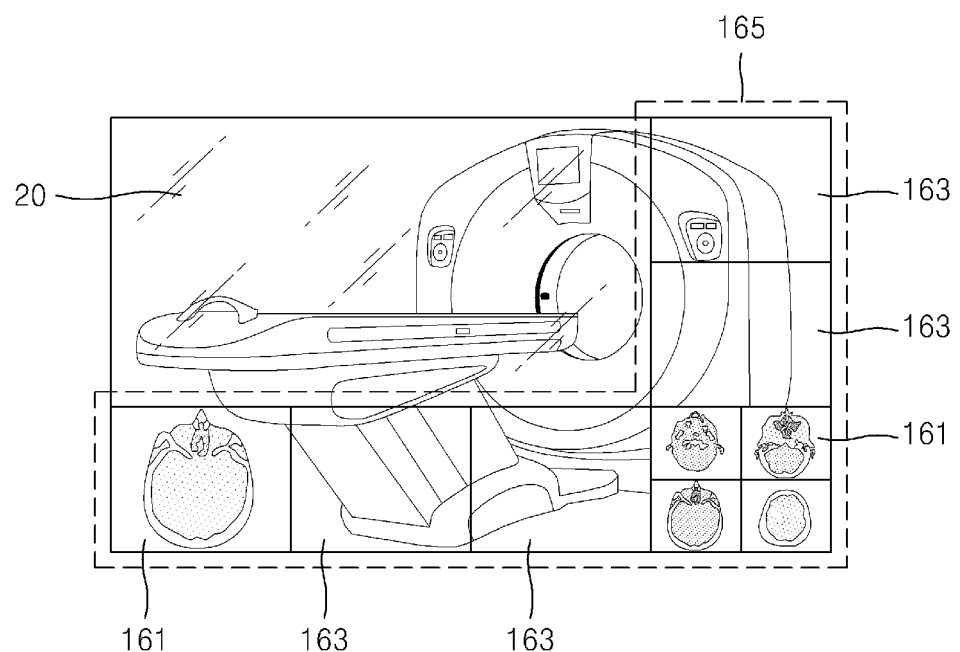
Figure 3C:
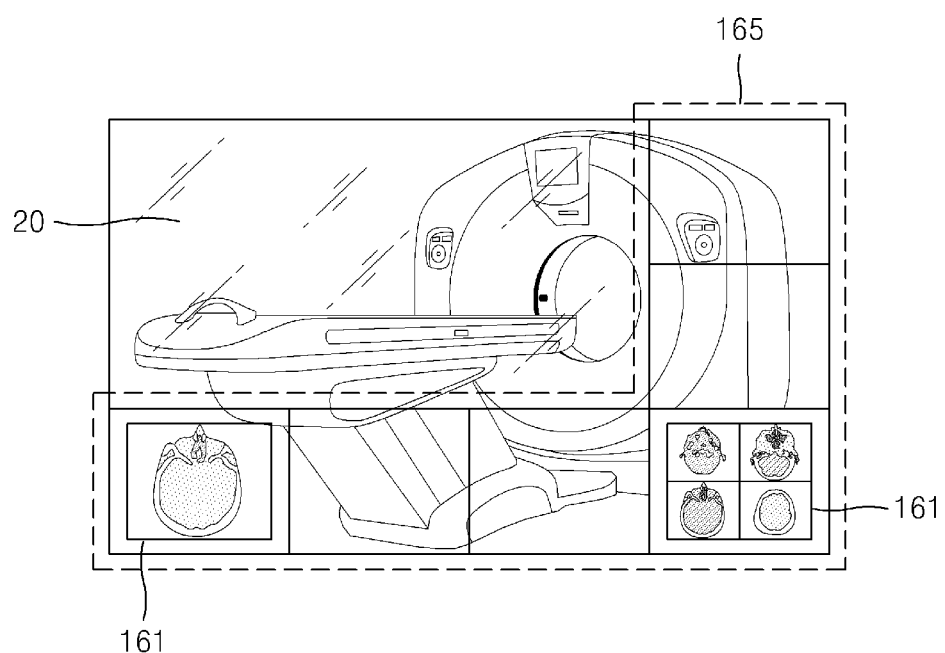
Figure 3D:
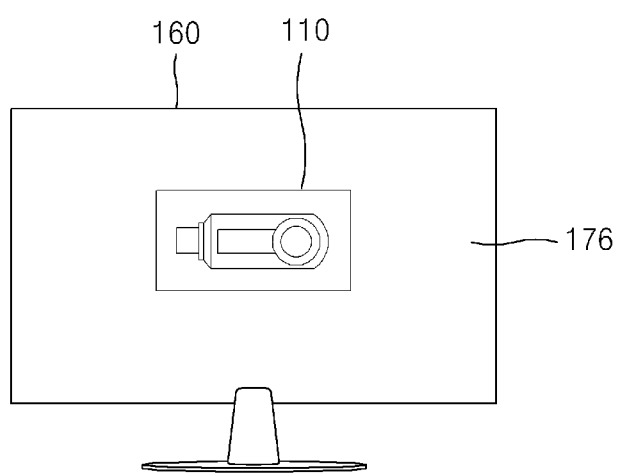

As shown in FIG. 3D, medical information providing apparatus 100 may include the image obtainer 110 at a back side 176 of the display 160. The image obtainer 110 may capture a room inside image, and the medical information providing apparatus 100 may include one or more image obtainers 110 that correspond to one or more of the displays 160, respectively. That is, the medical information providing apparatus 100 may include the image obtainer 110 at a back side 176 of each of the displays 160.

In another exemplary embodiment, the medical information providing apparatus 100 may include the image obtainers 110 that correspond to some of the displays 160. That is, in an exemplary embodiment shown in FIGS. 3A to 3C, the image obtainers 110 may be arranged at back sides of only four of the displays 160 that are horizontally arranged from among sic of the displays 160 marked by a dotted line 165. Alternatively, the image obtainer 110 may be disposed at a back side of only one display 160.

In the first mode of FIG. 3A, the medical information providing apparatus 100 provides, to the display 160, the shield room inside image which is captured by the image obtainer 110. The medical information providing apparatus 100 sets a virtual region inside the shield room that the operator 5 can view the room with the naked eye via a space in which the specific display 160 is disposed, and then sets a partial or entire region that corresponds to the virtual region of the shield room inside image. Afterward, the medical information providing apparatus 100 may provide a selected region to the specific display 160.

In the example shown in FIG. 3A, six displays 160 that are marked by the dotted line 165 display the shield room inside image which is captured while six displays 160 operate in the first mode.

The medical information providing apparatus 100 captures and provides the shield room inside image via the displays 160 disposed adjacent to the console room window 20. Accordingly, the medical information providing apparatus 100 may generate an effect by which the console room window 20 for observation inside the shield room is enlarged.

In the second mode of FIG. 3B, the medical information providing apparatus 100 obtains diagnostic information and outputs the diagnostic information via the display 160. The medical information providing apparatus 100 may provide, to the display 160, various types of diagnostic information including a medical image, a spread contrast medium image, a medical image capturing schedule list, or the like.

Referring to FIG. 1, a plurality of output devices (such as monitors, or the like) are separate from the console room window 20 in a console room. Thus, the operator 5 has difficulty in checking an image output on several monitors while the operator 5 performs the examination of the object 10.

The medical information providing apparatus 100, that operates in the second mode according to the present exemplary embodiment, outputs and displays the diagnostic information via the displays 160 that are disposed adjacent to the console room window 20, so that disruption of a view of the operator 5 is minimized while the object 10 is being images.

In the example shown in FIG. 3B two, displays 161 at lower left and lower right sides may operate in the second mode. That is, the displays 161 may obtain, as the diagnostic information, a medical image of the object 10, and may output and display the medical image. The rest of the displays 160 (reference numerals 163) may operate in the first mode and may output and display the shield room inside image.

In the third mode of FIG. 3C, the medical information providing apparatus 100 provides, to the display 160, both the shield room inside image and diagnostic information that is obtained from the medical diagnostic system 30.

In an exemplary embodiment, the medical information providing apparatus 100 may overlay the diagnostic information on the shield room inside image. In another exemplary embodiment, the medical information providing apparatus 100 may adjust transparency of the diagnostic information that is overlaid on the shield room inside image.

In the example shown in FIG. 3C, the displays 161 at lower left and lower right sides operate in the third mode. That is, the displays 161 may display both the shield room inside image and the diagnostic information, by overlaying the diagnostic information on the shield room inside image so that a portion of the shield room image is displayed simultaneously with the diagnostic information.

The medical information providing apparatus 100 may adjust a size of the diagnostic information. That is, in the example of the third mode shown in FIG. 3C, the medical information providing apparatus 100 may adjust the size of the diagnostic information that is overlaid on the shield room inside image and may display an image. This scaling of a region for display of the diagnostic information to within the circumference of the display device 160 may also be effected in the second mode. Even if the display is then set to function in the second mode (to show only the diagnostic information without transparency), a free peripheral edge surrounding diagnostic information can still be used to represent an additional portion of the shield room inside image or view. This could be referred to as the third mode, since both the shield room inside view or image and the diagnostic information are represented but without transparency of the diagnostic information. However, such a possibility could also be referred to as a second mode (because the diagnosis information is not transparent) with scaling of the diagnostic information and filling of a border edge with a portion of the shield room inside image or view. This goes to show that the skilled person should not interpret the modes described above to be strictly separate and divided, and some overlaps in modes may exist.

Figure 4:
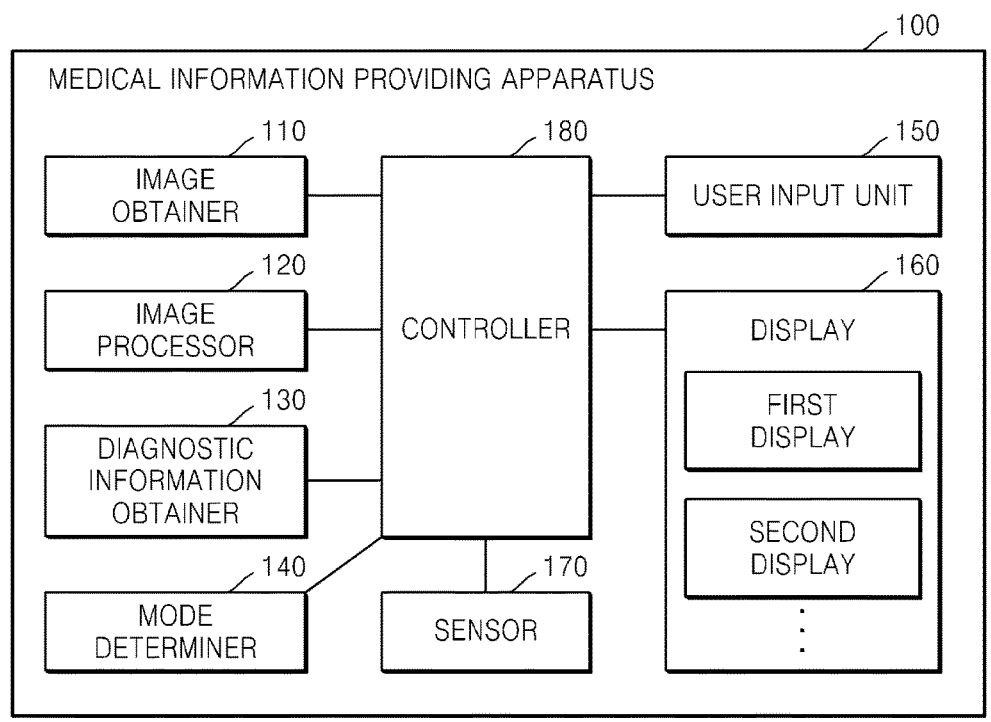
FIG. 4 is a block diagram of the medical information providing apparatus, according to an exemplary embodiment.

FIG. 4 is a block diagram of the medical information providing apparatus 100, according to an exemplary embodiment. The medical information providing apparatus 100 may include the image obtainer 110, a diagnostic information obtainer 130, and the display 160. And, the medical information providing apparatus 100 may further include an image processor 120, a mode determiner 140, a user input unit 150, a sensor 170, and a controller 180. However, not all shown elements are necessary elements. That is, the medical information providing apparatus 100 may be embodied with more or less elements than the shown elements.

The image obtainer 110 captures a room image of an inside of an examination room in which an object is positioned for medical examination. In detail, the image obtainer 110 captures a shield room inside image of the shield room in which the object 10 is positioned. A position and region inside the shield room that the image obtainer 110 captures may be adjusted by the user input unit 150 or the controller 180. For example, the image obtainer 110 may capture a specific position inside the shield room, based on a user input that is received by the user input unit 150.

The diagnostic information obtainer 130 obtains diagnostic information of the object.

The display 160 displays the diagnostic information which is overlaid on the room image according to the third mode.

The medical information providing apparatus 100 may include one or more image obtainers 110 that correspond to the displays 160, respectively. In another exemplary embodiment, the medical information providing apparatus 100 may be configured so that one image obtainer 110 corresponds to at least two displays 160.

Then, the image obtainer 110 of or for two displays 160 may be associated with one of two displays 160. Exemplary embodiments of the present disclosure encompass configurations with as many image obtainers 110 as displays 160, or less or more. The each of image obtainers 110 is associated with one of the displays in the above described exemplary embodiment, but more than one of the displays 160 can be associated with a single image obtainer 110 and the image obtainer 110 can be arranged separate from the displays 160, particularly inside the shield room or behind a small window between the console room and the shield room. Such an embodiment with camera separate from the display units allows the display units to be arranged on a wall next or adjacent to the physical boundaries of the window, to allow an operator to observe a larger observable area, than the area that could have been observed through the window alone.

That is, in the exemplary embodiments shown in FIGS. 2 and 3, the medical information providing apparatus 100 includes one image obtainer 110, but exemplary embodiments of the present disclosure are not necessarily limited thereto; the medical information providing apparatus 100 may include a plurality of the image obtainers 110 as in exemplary embodiments to be described later with reference to FIGS. 11 through 13.

In an exemplary embodiment, the image obtainer 110 may be disposed at a back side of the display 160. As illustrated in FIG. 3D, the image obtainer 110 may be attached at a center of the back side of the display 160 and may capture the shield room inside image.

In another exemplary embodiment, the image obtainers 110 may be disposed at several positions at a back side of the console room window 20. For example, the image obtainers 110 may be respectively disposed at back sides of the displays 160 that are arrayed in one direction at a lower end of the console room window 20. In another exemplary embodiment, the image obtainer 110 may be disposed at a corner of the console room window 20. However, exemplary embodiments are not limited thereto; thus, the image obtainers 110 may be disposed in various arrangements and may capture the shield room inside image.

The image obtainer 110 may include an infrared camera, a high-speed camera, a wide viewing angle camera, or the like, and may obtain a still image and/or a moving picture of the inside of the shield room.

The image processor 120 generates a shield room inside image to be displayed on the display 160.

The image processor 120 may select a partial or entire region of the shield room inside image. For example, when the medical information providing apparatus 100 includes a smaller number of the image obtainers 110 than a number of the displays 160, the image processor 120 may select a partial region of the shield room inside image that is captured by the image obtainers 110, and an image of the partial region is to be displayed on the displays 160.

In another exemplary embodiment, when the medical information providing apparatus 100 includes the image obtainers 110 that correspond to the displays 160, respectively, the image processor 120 may generate the shield room inside image and may select an entire region of the shield room inside image as a region to be displayed on the displays 160. On the other hand, the image processor 120 may select a partial region by editing or adjusting the shield room inside image.

In the present exemplary embodiment, the image processor 120 may select a partial region of the shield room inside image is to be provided to the display 160, according to various criteria. For example, the image processor 120 may select the partial region, based on a position of the display 160, that is to display the shield room inside image, on the console room window 20. In a case of the display 160 that is disposed at a lower right corner on the console room window 20, the image processor 120 may select a lower right partial region of the shield room inside image.

The image processor 120 may select a partial region, in consideration of an arrangement of the displays 160. That is, when the displays 160 are horizontally arrayed in one direction, the image processor 120 may horizontally divide the shield room inside image and then may select a plurality of partial regions. On the other hand, as illustrated in FIGS. 3A to 3C, when the displays 160 are arrayed in an L-shape, the image processor 120 may divide the shield room inside image into the L-shape and then may select a plurality of partial regions.

In another exemplary embodiment, the image processor 120 may detect a current position of the operator 5 and may select a partial region according to the position of the operator 5. That is, when the operator 5 is positioned at a right side with respect to a center of the console room window 20, the image processor 120 may select the partial region by referring to a direction of a view of the operator 5 with respect to the console room window 20. This will be described in detail below with reference to FIGS. 9 through 11.

However, exemplary embodiments are not limited thereto. The image processor 120 may select a partial or entire region of the shield room inside image according to various criteria. Also, the image processor 120 may select a region by simultaneously referring to several criteria, instead of just one criterion.

The diagnostic information obtainer 130 obtains diagnostic information related to the object 10 including various types of information that are used in diagnosing the object 10.

The diagnostic information obtainer 130 may obtain the diagnostic information from the medical diagnostic system 30 or an external server. For example, the diagnostic information obtainer 130 may obtain a medical image obtained by imaging the object 10, as the diagnostic information, from the medical diagnostic system 30. In another exemplary embodiment, the diagnostic information obtainer 130 may obtain the diagnostic information about personal information or a medical image capturing schedule of a patient from a hospital server.

The diagnostic information obtainer 130 may communicate with the medical diagnostic system 30 or the external server via a wireless or wired network, so that the diagnostic information obtainer 130 may obtain the diagnostic information. In the present exemplary embodiment, the diagnostic information obtainer 130 may exchange data with the hospital server or other medical apparatuses in a hospital connected via a Picture Archiving and Communication System (PACS). Also, the diagnostic information obtainer 130 may perform data communication according to a Digital Imaging and Communications in Medicine (DICOM) standard.

The diagnostic information obtainer 130 may include one or more elements for enabling communication with an external device. For example, the diagnostic information obtainer 130 may include a short-distance communication module, a wired communication module, and a mobile communication module.

The short-distance communication module is a module for short-distance communication within a predetermined distance. Examples of the short-distance communication module may include, but are not limited to, wireless LAN, Wi-Fi, Bluetooth, Zigbee, Wi-Fi Direct (WFD), ultra wideband (UWB), infrared Data Association (IrDA), Bluetooth Low Energy (BLE), and Near Field Communication (NFC).

The wired communication module is a module for communication using an electrical signal or an optical signal. Examples of a wired communication technology may include a pair cable, a coaxial cable, an optical fiber cable, an Ethernet cable, or the like.

The wireless communication module exchanges a wireless signal with at least one of a base station, an external terminal, and a server in a mobile communication network. The wireless signal may include various types of data according to a voice call signal, a video call signal, or an exchange of text or multimedia message.

The mode determiner 140 determines a medical information providing mode of the medical information providing apparatus 100 according to a type of medical information that is output by the medical information providing apparatus 100 via the display 160.

That is, the medical information providing mode may include the first mode for providing the shield room inside image to the displays 160, the second mode for providing the diagnostic information to the displays 160, and the third mode for providing both the shield room inside image and the diagnostic information to the displays 160. The display may be transparent in a first mode to present a direct shield room inside view to the user or operator, without using any image obtainer 110. In the third mode, the displayed diagnostic information may then be presented in a transparent fashion to still offer the direct shield room inside view (instead of the shield room inside image obtained with one or more of the image obtainers 110), resulting in combined or aggregated third display mode of the first and second display modes together, wherein the first and third display modes are in fact based on a transparency effect of the displays, to allow the operator to see a shield room inside view, optionally through displayed diagnostic information, instead of actually displayed shield room inside images from any image obtainers. In exemplary embodiments, the observable area is enlarged relative to the area of the window, which remains after arranging the displays on or in the window.

In the present exemplary embodiment, the mode determiner 140 may determine the medical information providing mode as diagnostic with respect to the object 10. The diagnostic mode with respect to the object 10 may include all processes that are performed by the medical diagnostic system 30 with respect to the object 10, and examples of the processes include a process of obtaining medical information about the object 10, a process of capturing a medical image, a process of providing medical information, a process of ending the provision of the medical information according to feedback from the operator 5, or the like.

In more detail with reference to an MRI system, the diagnostic mode with respect to the object 10 may include a process of checking whether any particular factor (e.g., whether a contrast medium is used) exists in capturing an MRI image, in consideration of patient information about the object 10, a process of guiding the object 10 to be disposed on a diagnostic table of the MRI system, a process of capturing the MRI image, a process of outputting the captured MRI image, or the like. Here, the aforementioned processes are merely an example of the diagnostic mode performed by the medical diagnostic system 30; thus, exemplary embodiments are not limited thereto.

In relation to the MRI system, the mode determiner 140 may determine the medical information providing mode as each of the processes in the MRI system is performed. That is, whenever the diagnostic process of the MRI system proceeds, a type of medical information to be output is changed, and the mode determiner 140 may determine the medical information providing mode.

For example, when a diagnostic mode with respect to a new patient proceeds in the MRI system, and the diagnostic information obtainer 130 obtains patient information about the new patient, the mode determiner 140 may determine the medical information providing mode as the second mode or the third mode, so that the display 160 may output the patient information as the diagnostic information.

Accordingly, when the MRI capturing is ended and the diagnostic information obtainer 130 obtains an MRI image, the mode determiner 140 may determine the medical information providing mode. At the same time, the mode determiner 140 may maintain the medical information providing mode of the display 160 that operates according to the second mode or the third mode and output the patient information. That is, the mode determiner 140 may separately determine the medical information providing modes of the displays 160.

In the present exemplary embodiment, the mode determiner 140 may determine the medical information providing mode according to an increase in a number of pieces of diagnostic information obtained by the diagnostic information obtainer 130. In another exemplary embodiment, the mode determiner 140 may determine the medical information providing modes of the displays 160 according to priority orders set in the displays 160. This will be described in detail with reference to FIGS. 15 through 19.

The user input unit 150 is a unit by which the operator 5 inputs data to control the medical information providing apparatus 100. For example, the user input unit 150 may include, but is not limited to, a keyboard, a mouse, a dome switch, a touch pad (a touch capacitive type touch pad, a pressure resistive type touch pad, an infrared beam sensing type touch pad, a surface acoustic wave type touch pad, an integral strain gauge type touch pad, a piezo effect type touch pad, or the like), a jog wheel, a jog switch, or the like. In particular, when the touch pad and a display panel form a mutual layer structure, this structure may be called a touch screen. For instance, in FIG. 2, a single keyboard is shown. In this case, an MRI/CT console room space utilization can be maximized, as compared to the related art apparatus of FIG. 1, wherein each monitor or screen is connected to an associated computer or the like, having individual input means, such as keyboards and mice. According to exemplary embodiments of the present disclosure, multiple related art monitors, screens or display units can be combined and/or integrated, to be driven by a single computer or the like, needing only a singular user input unit 150 or only one set thereof (mouse+keyboard). Therein, the window and the at least one display unit 160 are driven in combination, i.e., furnished with display data from a single source (the relevant computer or the like). The user input unit 150 may detect an actual touch and/or a proximate touch.

The user input unit 150 may detect a touch input (e.g., a touch and hold input, a tap input, a double-tap input, a flick input, or the like) with respect to the output medical information. Also, the user input unit 150 may detect a drag input from a point in which the touch input is detected. The user input unit 150 may detect multiple touch inputs (e.g., a pinch) with respect to at least two points of the medical information.

The medical information providing apparatus 100 may include the user input unit 150 that commonly corresponds to the displays 160 and commonly receives user inputs for controlling the displays 160. This will be described in detail with reference to FIG. 20.

The display 160 displays and outputs information that is processed in the medical information providing apparatus 100. The display 160 may display the shield room inside image or may display the diagnostic information obtained from the medical diagnostic system 30. For example, the display 160 may display various information such as the shield room inside image, the medical image, the medical image capturing schedule, or the like. Also, the display 160 may overlay the diagnostic information on the shield room inside image and then may display these images together.

When the touch pad and the display 160 form a layer structure, and thus are formed as a touch screen, the display 160 may be used as both an output device and an input device. The display 160 may include at least one of a liquid crystal display (LCD), a thin film transistor-liquid crystal display (TFT-LCD), an organic light-emitting display (OLED), a flexible display, a three-dimensional (3D) display, and/or an electrophoretic display. The medical information providing apparatus 100 may include two or more displays 160.

The display 160 may be disposed adjacent to the console room window 20 and may output the shield room inside image. Accordingly, the operator 5 of the medical information providing apparatus 100 may observe an area inside the shield room, which is larger than an observation area that the console room window 20 may provide. That is, the medical information providing apparatus 100 may generate an effect by which the console room window 20 is enlarged. And more of the shield room is made visible to the operator on the displays 160 in combination with a remainder of the console room window 20 with the displays on or against this window 20 to allow a direct shield room inside view or display obtained shield room inside images, or with the displays 160 arranged at least partially outside the peripheral circumference of the window 20 to display obtained shield room inside images.

Here, the fact that the display 160 is disposed adjacent to the console room window 20 may mean that an end surface of the console room window 20 and an end surface of the display 160 physically and completely meet each other. However, exemplary embodiments are not limited thereto; thus, the end of the console room window 20 and the end of the display 160 may be separated from each other within a predetermined distance by having, but not being limited to, a substance, a structure, or a material disposed therebetween, which may shield the console room window 20 from the shield room. The medical information providing apparatus 100 may be embodied so that the predetermined distance may be at a minimum to maximize the effect of enlarging the console room window 20.

In another exemplary embodiment, priority orders may be set in the displays 160. The priority orders may be differently set in the displays 160 or the same priority order may be set in every two or more displays 160. The displays 160 may sequentially output diagnostic information according to the set priority orders. This will be described in detail with reference to FIGS. 17 through 19.

The sensor 170 senses the operator 5 of the medical information providing apparatus 100. The sensor 170 may sense a position of the operator 5, e.g., a distance between the operator 5 and the console room window 20 or between the operator 5 and the display 160. In order to sense the operator 5, the sensor 170 may include various sensors such as a depth sensor, a distance sensor, a motion recognition sensor, a device recognition sensor, a voice recognition sensor, an ID signal detection sensor, or the like.

The sensor 170 may also sense a view or a gesture of the operator 5 by using an iris recognition sensor or a camera. This will be described in detail with reference to FIGS. 9 through 11.

The controller 180 controls operations of the medical information providing apparatus 100. For example, the controller 180 may provide, to the display 160, the shield room inside image that is captured by the image obtainer 110 and the diagnostic information that is obtained by the diagnostic information obtainer 130. Also, the controller 180 may provide the medical information to the display 160 according to the medical information providing mode. In addition the controller 180 may control the image processor 120 to select a partial region of the shield room inside image based on the sensed user 5.

That is, the controller 180 may control operations of the image obtainer 110, the image processor 120, the diagnostic information obtainer 130, the mode determiner 140, the user input unit 150, the display 160, and the sensor 170 that are included in the medical information providing apparatus 100.

Figure 5:
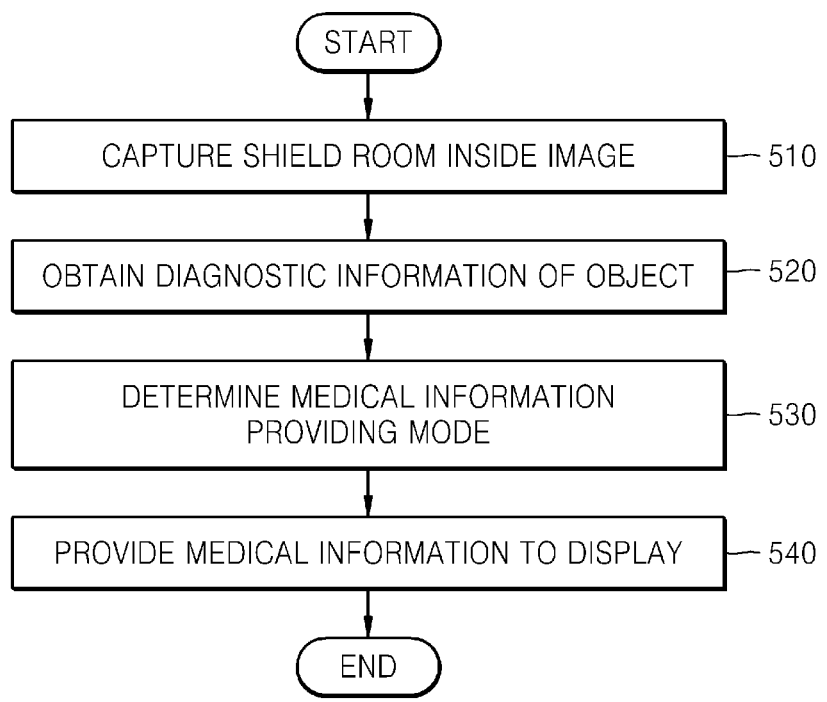
FIG. 5 is a flowchart of a medical information providing method, according to an exemplary embodiment.

FIG. 5 is a flowchart of a medical information providing method, according to an exemplary embodiment. The flowcharts shown in FIGS. 5 and 6 include operations that are processed by the medical information providing apparatus 100, the image obtainer 110, the image processor 120, the diagnostic information obtainer 130, the mode determiner 140, the user input unit 150, the display 160, and the sensor 170 that are described with reference to FIG. 4. Thus, hereinafter, although descriptions are omitted, if the descriptions are related to the elements and structures shown in FIG. 4, the descriptions may also be applied to the flowcharts of FIGS. 5 and 6.

In operation 510, the medical information providing apparatus 100 captures a shield room inside image. The medical information providing apparatus 100 may capture the shield room inside image by using at least one image obtainer disposed at a back side of a display or a console room window.

In the present exemplary embodiment, when a plurality of the displays captures images of the inside of the shield room, the displays may capture images of overlapping regions inside the shield room. However, the displays may capture images of regions inside the shield room, which are separate from each other. This will be described in detail with reference to FIG. 13.

In operation 520, the medical information providing apparatus 100 obtains diagnostic information related to an object. The diagnostic information may be obtained from a medical diagnostic system connected to the medical information providing apparatus 100 via a network. Alternatively, the diagnostic information may be obtained from an external server that is connected to the medical information providing apparatus 100.

The medical information providing apparatus 100 may obtain the diagnostic information that is generated as diagnostic mode with respect to the object starts and proceeds. That is, the medical information providing apparatus 100 may obtain new diagnostic information whenever diagnostic processes with respect to objects are performed.

In operation 540, the medical information providing apparatus 100 provides medical information via the display. In detail, in operation 540, the medical information providing apparatus 100 displays the diagnostic information which is overlaid on the room image according to the third mode, on the display 160.

The medical information providing method according to an exemplary embodiment may further include operation 530 after the operation 520. In operation 530, the medical information providing apparatus 100 determines a medical information providing mode. Since the medical information providing apparatus 100 obtains the diagnostic information, the medical information providing apparatus 100 may change a first mode for displaying the shield room inside image into a second mode or a third mode. That is, after the medical information providing apparatus 100 obtains the diagnostic information, the medical information providing apparatus 100 may change the medical information providing mode that is the first mode, so as to output the diagnostic information to the display.

On the contrary, the medical information providing apparatus 100 may change a medical information providing mode of the display, which outputs the diagnostic information in the second mode or the third mode, into the first mode so that the display may discontinue the output of the diagnostic information and then may output the shield room inside image.

In another exemplary embodiment, when the medical information providing apparatus 100 includes a plurality of the displays, the medical information providing apparatus 100 may change medical information providing modes of the displays so that the diagnostic information that is displayed on one of the displays may be transferred and displayed on another display. That is, the medical information providing apparatus 100 may change the medical information providing mode of a display, which displays the diagnostic information, into the first mode, and the medical information providing mode of a display, which is to display the diagnostic information, into the second mode or the third mode.

The second mode and the third mode are distinguished therebetween according to whether the display displays the shield room inside image along with the diagnostic information. When the medical information providing apparatus 100 displays the diagnostic information on one of the displays, the second mode and the third mode may be determined according to a user input that selects one of the second mode and the third mode. Alternatively, the medical information providing apparatus 100 may select the second mode or the third mode and then may display the diagnostic information.

In operation 540, the medical information providing apparatus 100 provides medical information via the display.

The medical information providing apparatus 100 provides the shield room inside image, the diagnostic information, or both the shield room inside image and the diagnostic information to the display, according to the medical information providing mode determined in operation 530. The medical information providing apparatus 100 may provide the medical information according to the medical information providing modes that are set in the respective displays.

When the medical information providing apparatus 100 obtains new diagnostic information in addition to the medical information displayed on the display, the medical information providing apparatus 100 repeatedly performs operations 520 through 540. That is, the medical information providing apparatus 100 may newly determine medical information providing modes of one or more displays according to the new diagnostic information, and may display and output the medical information according to the newly determined medical information providing modes.

Figure 6:
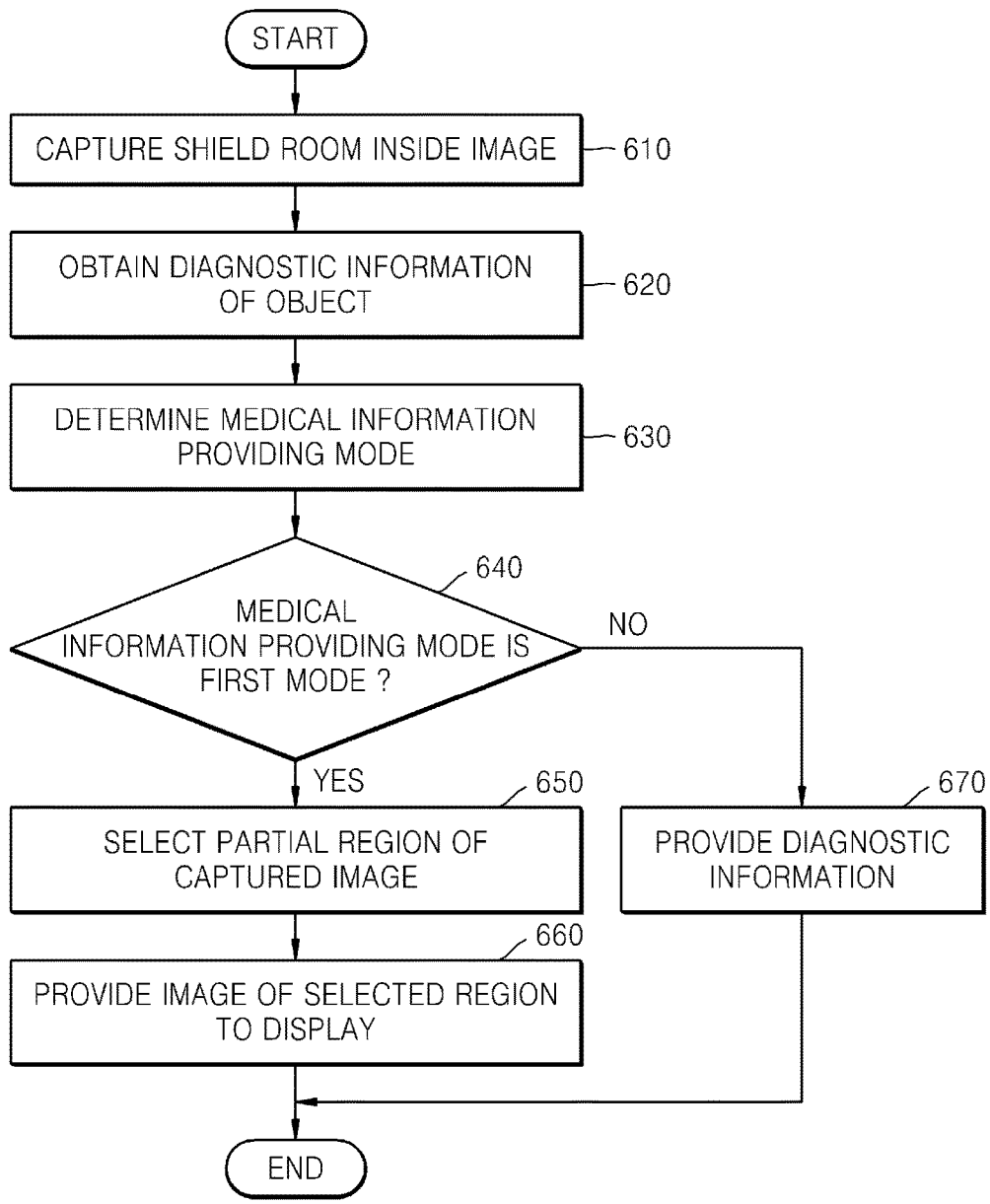
FIG. 6 is a flowchart of a medical information providing method, according to another exemplary embodiment.

FIG. 6 is a flowchart of a medical information providing method, according to another exemplary embodiment. Operations 610 through 630 are similar to operations 510 through 530 that are described with reference to FIG. 5; thus, although descriptions are omitted, if the descriptions are described with reference to FIG. 5, the descriptions may also be applied to operations 610 through 630 of FIG. 6.

In operation 610, the medical information providing apparatus 100 may capture a shield room inside image by using at least one image obtainer. In operation 620, the medical information providing apparatus 100 obtains diagnostic information related to an object. In operation 630, the medical information providing apparatus 100 determines a medical information providing mode of at least one display.

In operation 640, the medical information providing apparatus 100 determines whether the medical information providing mode of the display is a first mode. When the medical information providing mode of the corresponding display is the first mode, the method proceeds to operation 650. When the medical information providing mode of the corresponding display is a second mode or a third mode, the method proceeds to operation 670.

In operation 650, the medical information providing apparatus 100 selects a partial region of the shield room inside image that is captured in operation 610. Alternatively, to achieve the first mode, the displays 160 can be made transparent to present to the operator a direct shield room inside view into the shield room through the transparent displays in the first mode.

As described with reference to FIG. 4, the medical information providing apparatus 100 may select some of or the entire region of the shield room inside image according to a 1:1 matching relation between the image obtainers and the displays.

In more detail, when the image obtainers and the displays have the 1:1 matching relation, the medical information providing apparatus 100 displays the shield room inside image, which is captured by the image obtainers, on the displays. However, although the image obtainers and the displays have the 1:1 matching relation, the medical information providing apparatus 100 may select a partial region of the shield room inside image by referring to a relation with an operator such as an operator's position, an operator's view, or the like.

Also, neighboring displays are to present mutually complementary portions of shield room inside images, mostly without overlap or double representation, for which the selection of partial regions of the shield room inside images obtained by separate image obtainers associated with distinct displays may also be used. Likewise, appropriate image processing may be applied to present a shield room inside view from an altering perspective of the operator 5, for instance when the operator moves in the console room. The image processing may then be directed at changing the perspective of the shield room inside image, presented on the displays 160, to correspond with the view that the operator 5 has into the shield room directly through the window 20, which is the shield room inside view.

When the image obtainers and the displays do not have the 1:1 matching relation, the medical information providing apparatus 100 may select a partial region of the shield room inside image and may display an image of the partial region on the display. That is, the medical information providing apparatus 100 may select a display-target partial region of the shield room inside image according to an arrangement and position of the display. This will be described in detail with reference to FIGS. 12 and 13.

In operation 660, the medical information providing apparatus 100 provides, to the display, an image of the region that is selected in operation 650. That is, the medical information providing apparatus 100 may provide the shield room inside image of the region selected in operation 650, by displaying the shield room inside image on the display.

In operation 670, the medical information providing apparatus 100 provides diagnostic information via the display. That is, when the medical information providing mode is the second mode or the third mode, the medical information providing apparatus 100 may display and output the diagnostic information that is obtained in operation 620.

In the second mode, the medical information providing apparatus 100 outputs only the diagnostic information to the display, whereas the medical information providing apparatus 100 outputs the diagnostic information along with the shield room inside image in the third mode. In the third mode, the medical information providing apparatus 100 may overlap the diagnostic information on the shield room inside image and may display them. In embodiments based on transparent displays 160, the presentation of the diagnostic information can be made partially transparent, to allow the operator to see directly into the shield room through the display and the diagnostic information displayed thereon.

Figure 7:
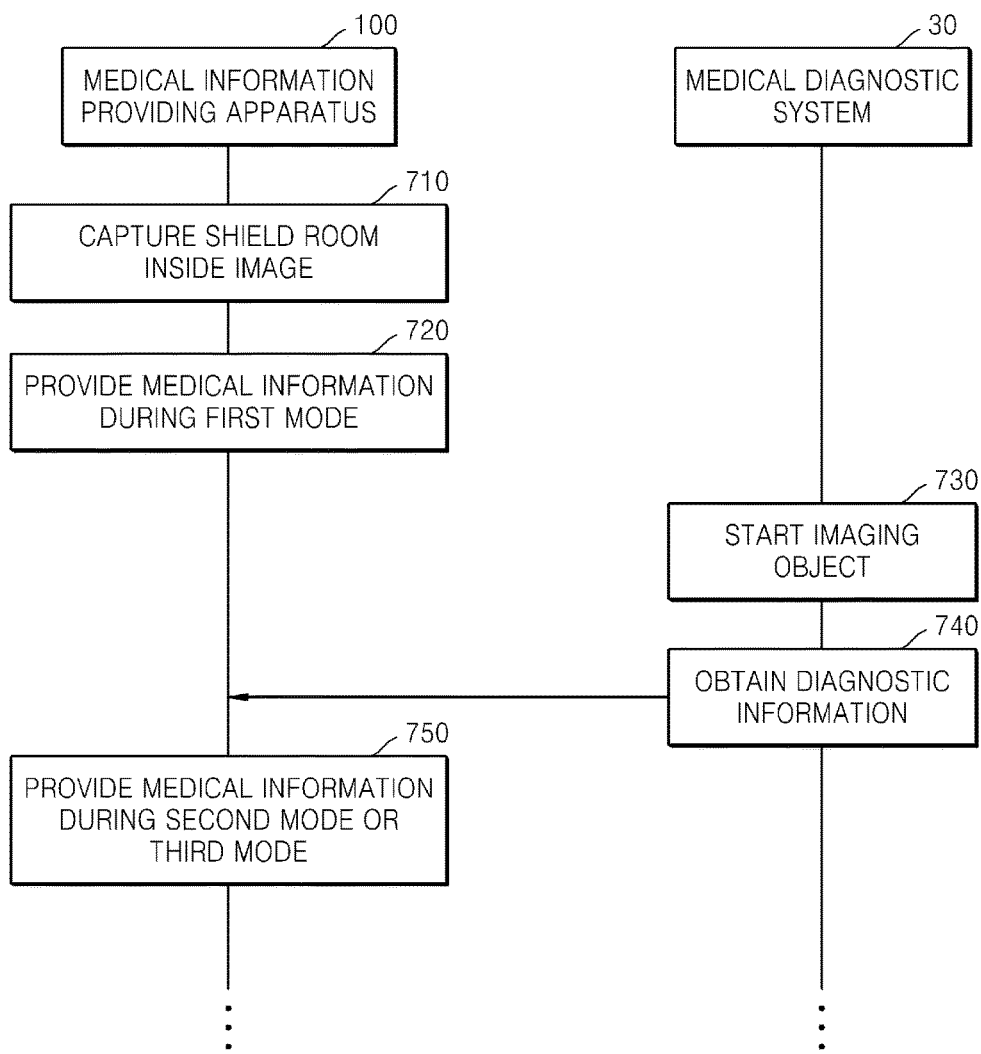
FIG. 7 illustrates operations between the medical information providing apparatus and the medical diagnostic system, according to an exemplary embodiment.

FIG. 7 illustrates operations between the medical information providing apparatus 100 and the medical diagnostic system 30, according to an exemplary embodiment.

In operation 710, the medical information providing apparatus 100 captures a shield room inside image. This operation is the same as that described with reference to FIGS. 5 and 6; thus, detailed descriptions thereof will be omitted here.

In operation 720, the medical information providing apparatus 100 provides medical information during a first mode. That is, the medical information providing apparatus 100 outputs the shield room inside image, which is captured in operation 710, via a display.

As described with reference to FIG. 6, the medical information providing apparatus 100 may select a partial region of the shield room inside image and may display an image of the selected partial region on the display.

In operation 730, the medical diagnostic system 30 starts imaging an object. That is, the medical diagnostic system 30 performs a diagnostic process with respect to the object. As described with reference to FIG. 4, the diagnostic process may include all of the processes that the medical diagnostic system 30 may perform with respect to the object.

In operation 740, the medical information providing apparatus 100 obtains diagnostic information from the medical diagnostic system 30. The medical information providing apparatus 100 may receive the diagnostic information, by wired or wireless connection, from the medical diagnostic system 30. The medical information providing apparatus 100 may obtain the diagnostic information from an external server.

In operation 750, the medical information providing apparatus 100 determines a medical information providing mode as a second mode or a third mode, and then provides the medical information. That is, in order to display the diagnostic information obtained in operation 740, the medical information providing apparatus 100 may change the medical information providing mode from the first mode to the second mode or the third mode.

The medical information providing apparatus 100 may display the diagnostic information on the display according to the determined medical information providing mode. As described above, the medical information providing apparatus 100 may display only the diagnostic information in the second mode, and may display both the diagnostic information and the shield room inside image in the third mode.

Figure 8:
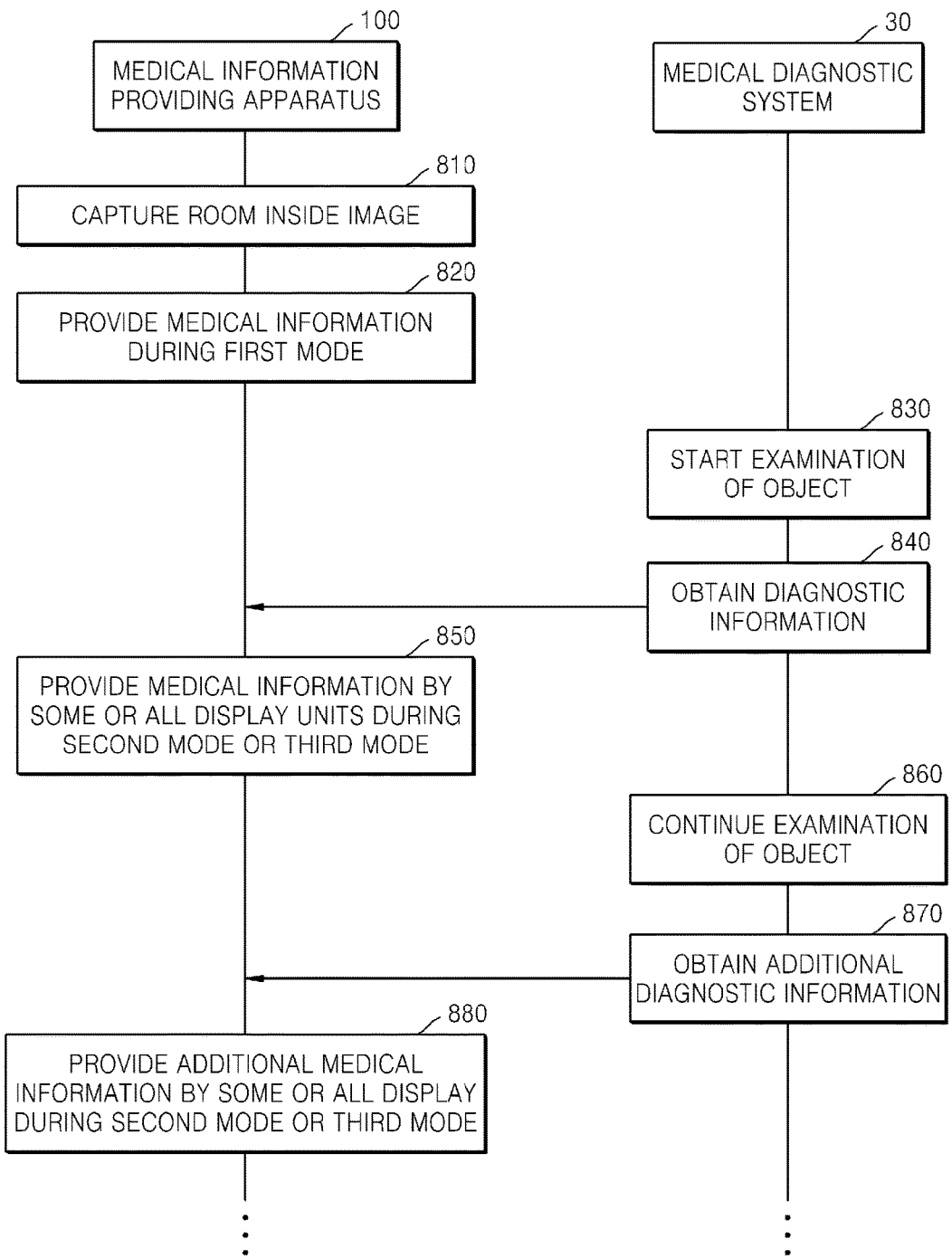
FIG. 8 illustrates operations between the medical information providing apparatus and the medical diagnostic system, according to another exemplary embodiment.

FIG. 8 illustrates operations of the medical information providing apparatus 100 and the medical diagnostic system 30, according to another exemplary embodiment.

In an exemplary embodiment of FIG. 8, the medical information providing apparatus 100 includes a plurality of displays.

In operation 810, the medical information providing apparatus 100 captures a shield room inside image. In operation 820, the medical information providing apparatus 100 provides the shield room inside image in a first mode. That is, the medical information providing apparatus 100 of FIG. 8 determines a medical information providing mode of at least one of the displays as the first mode, and displays the shield room inside image.

In operation 830, the medical diagnostic system 30 starts imaging an object, and in operation 840, the medical information providing apparatus 100 obtains diagnostic information from the medical diagnostic system 30.

In operation 850, the medical information providing apparatus 100 determines the medical information providing mode of at least one of the displays as a second mode or a third mode. Afterward, the medical information providing apparatus 100 may display the diagnostic information on the display whose medical information providing mode is determined as the second mode or the third mode.

The medical information providing apparatus 100 may determine medical information providing modes of some or all of the displays as the second mode or the third mode, in consideration of a type of the diagnostic information obtained in operation 840, and a number of pieces of diagnostic information to be displayed.

The medical information providing apparatus 100 may determine an order by which the medical information providing modes are changed from the first mode to the second mode or the third mode, based on priority orders that are set in the displays, respectively. That is, the medical information providing apparatus 100 may change the medical information providing modes according to higher priority orders, and may provide the diagnostic information on the displays whose medical information providing modes are changed.

In operation 860, the medical diagnostic system 30 continues the diagnostic process with respect to the object.

In operation 870, the medical information providing apparatus 100 additionally obtains the diagnostic information that is newly generated. The medical information providing apparatus 100 may obtain diagnostic information from the medical diagnostic system 30 and also from an external server.

In operation 880, the medical information providing apparatus 100 changes the medical information providing mode of at least one of the displays into the second mode or the third mode, and provides the additional diagnostic information. That is, in order to display and output the diagnostic information that is newly obtained in operation 870, the medical information providing apparatus 100 may change the medical information providing mode of at least one of the displays.

In operation 880, the medical information providing apparatus 100 may change the medical information providing mode of the display, which was outputting the diagnostic information during the second mode or the third mode in operation 850, into the first mode. For example, when the medical information providing apparatus 100 discontinues displaying the diagnostic information that is obtained in operation 840, the medical information providing apparatus 100 may change the medical information providing mode of the display, which outputs the diagnostic information of operation 840, into the first mode, and may change a medical information providing mode of another display to output the diagnostic information of operation 870 into the second mode or the third mode.

Figure 9:
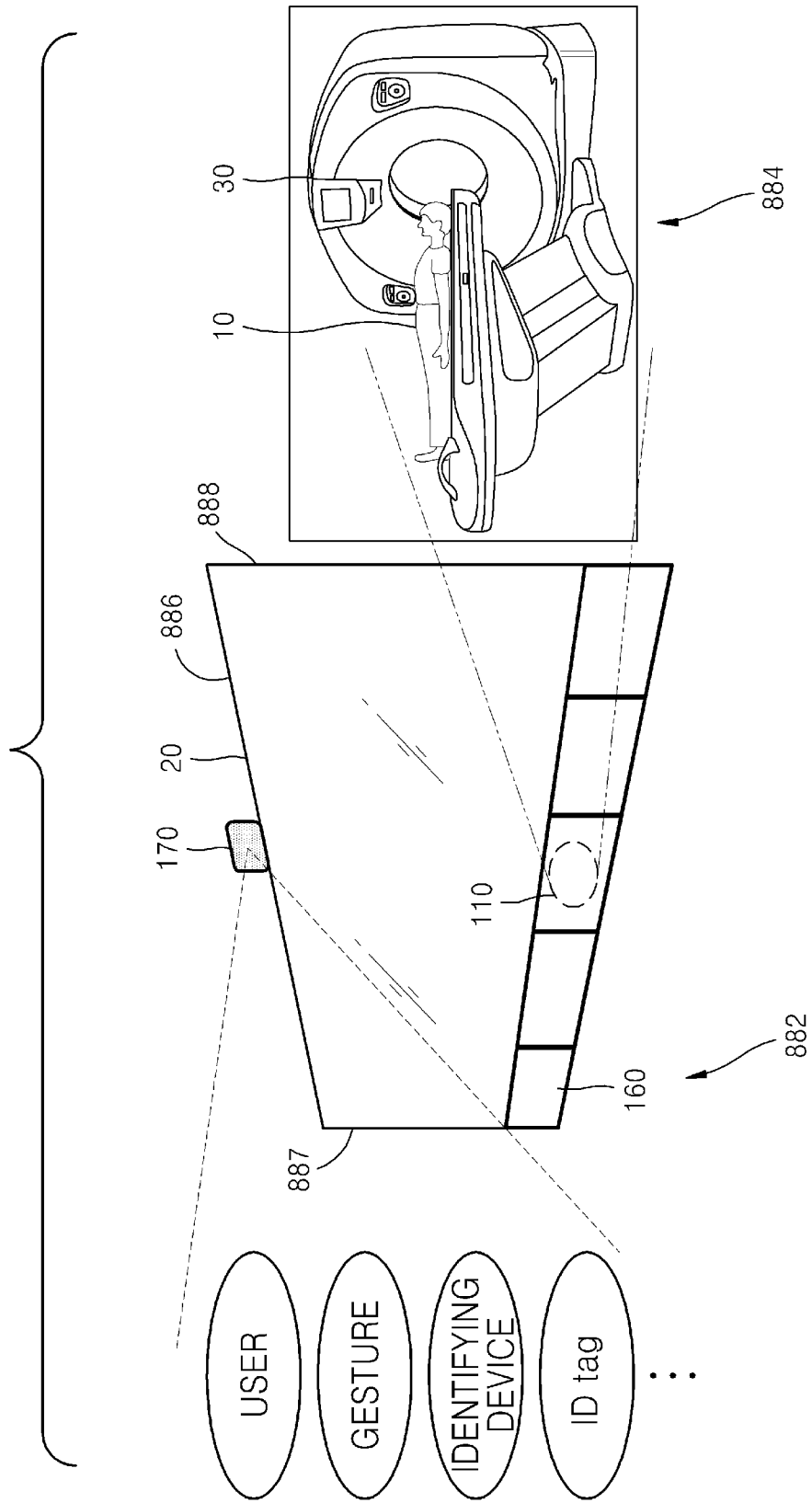
FIG. 9 illustrates an example of the medical information providing apparatus, according to an exemplary embodiment.

FIG. 9 illustrates an example in which the medical information providing apparatus 100 detects an operator, according to an exemplary embodiment.

Referring to FIG. 9, a left side and a right side with respect to the console room window 20 indicate a console room 882 and a shield room 884, respectively. In an exemplary embodiment of FIG. 9, the image obtainer 110, the display 160, and the sensor 170 are disposed adjacent to the console room window 20.

Referring to FIG. 9, the sensor 170 is disposed at a top end 886 of the console room window 20, but exemplary embodiments are not limited thereto. That is, the sensor 170 may be disposed at left and right sides 887, 888 of the console room window 20, or may be disposed in the console room, separately from the console room window 20.

The sensor 170 may include various sensor devices such as the depth sensor, the distance sensor, the motion recognition sensor, the device recognition sensor, the voice recognition sensor, the ID signal detection sensor, the iris recognition sensor, the camera, or the like.

The medical information providing apparatus 100 may detect a position and a distance of the operator from the display by using the sensor and also may detect sense the operator by recognizing a specific gesture.

In more detail, the medical information providing apparatus 100 may detect the position of the operator and the distance between the operator and the display by using the distance sensor or the depth sensor. The medical information providing apparatus 100 may recognize the specific gesture of the operator by using the motion recognition sensor, and may detect a position, in which the specific gesture is detected, as the position of the operator.

The medical information providing apparatus 100 may sense the ID device of the operator. The medical information providing apparatus 100 may detect the ID signal transmitted from the ID device, and may sense the position of the operator from a position of the ID device.

In the present exemplary embodiment, the medical information providing apparatus 100 may sense the ID device that is connected to the medical diagnostic system 30. For example, when an operator of the medical information providing apparatus 100 logs into the medical diagnostic system 30 to image an object, an ID device of the operator may include log-in information related to the medical diagnostic system 30. Accordingly, the medical information providing apparatus 100 may detect the operator by detecting the ID device that is logged into the medical diagnostic system 30.

In another exemplary embodiment, the medical information providing apparatus 100 may distinguish a specific operator from other operators in the console room. For example, when the plurality of operators have respective ID devices, the medical information providing apparatus 100 may sense an ID device that is connected to the medical diagnostic system 30 and may detect the specific operator who logs in the medical diagnostic system 30 to image the object.

In another exemplary embodiment, the medical information providing apparatus 100 may distinguish the specific operator by sensing a pre-stored specific gesture. That is, the medical information providing apparatus 100 may detect the plurality of operators in the console room by using the distance sensor and the depth sensor, and may detect an operator that takes a pre-set gesture, as the specific operator.

Figure 10:
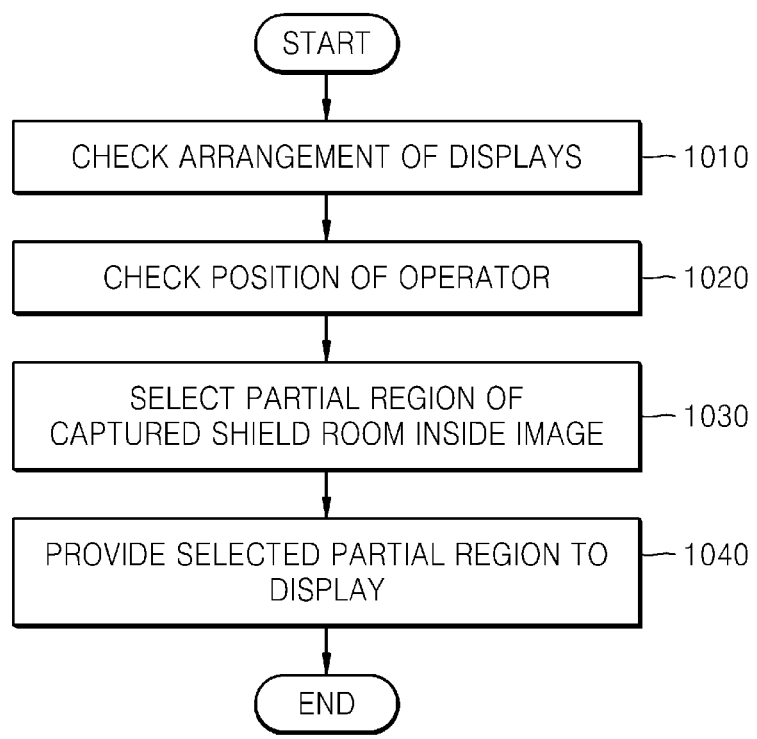
FIG. 10 is a flowchart of a method of selecting a partial region of an image of an inside of a room, according to an exemplary embodiment.

FIG. 10 is a flowchart of a method of selecting a partial region of a shield room inside image, according to an exemplary embodiment.

In operation 1010, the medical information providing apparatus 100 checks an arrangement of displays by receiving pre-stored information about an arrangement of displays. Also, the medical information providing apparatus 100 may receive a user input that decides an arrangement and positions of displays, and then may check the arrangement of the displays based on the user input.

In operation 1020, the medical information providing apparatus 100 checks the position of an operator by using the various methods described above with reference to FIG. 9.

In operation 1030, the medical information providing apparatus 100 selects the partial region of the shield room inside image. This selection may be accompanied by image processing and may be based on a perspective change of the operator looking into the shield room, as indicated above. When the medical information providing apparatus 100 selects the partial region to be displayed on the display, the medical information providing apparatus 100 may use a plurality of pieces of information that are checked in operations 1010 and 1020. In more detail, the medical information providing apparatus 100 may check the arrangement and positions of the displays and the position of the operator with respect to the console room window, so that the medical information providing apparatus 100 may effectively generate an effect of enlarging the console room window view.

For example, for a case in which the display is disposed adjacent to a right side 888 of the console room window, and for a case in which the display is disposed adjacent to a left side 887 of the console room window, the medical information providing apparatus 100 has to provide different images to an operator who is positioned at a center in front of the console room window. That is, the medical information providing apparatus 100 may select the partial region of the shield room inside image, in consideration of the arrangement and positions of the displays.

As another example, a view of an operator who is positioned at a left side of the console room window and who watches inside the console room window is different from a view of an operator who is positioned at a right side of the console room window and who watches inside the console room window. Accordingly, the medical information providing apparatus 100 may check an operator's position when the medical information providing apparatus 100 selects the partial region of the shield room inside image which is to be displayed on the display.

In operation 1040, the medical information providing apparatus 100 provides, to the display, the image of the partial region of the shield room inside image that is selected in operation 1030. Accordingly, the medical information providing apparatus 100 may provide the effect of enlarging the console room window view with respect to the operator.

Figure 11:
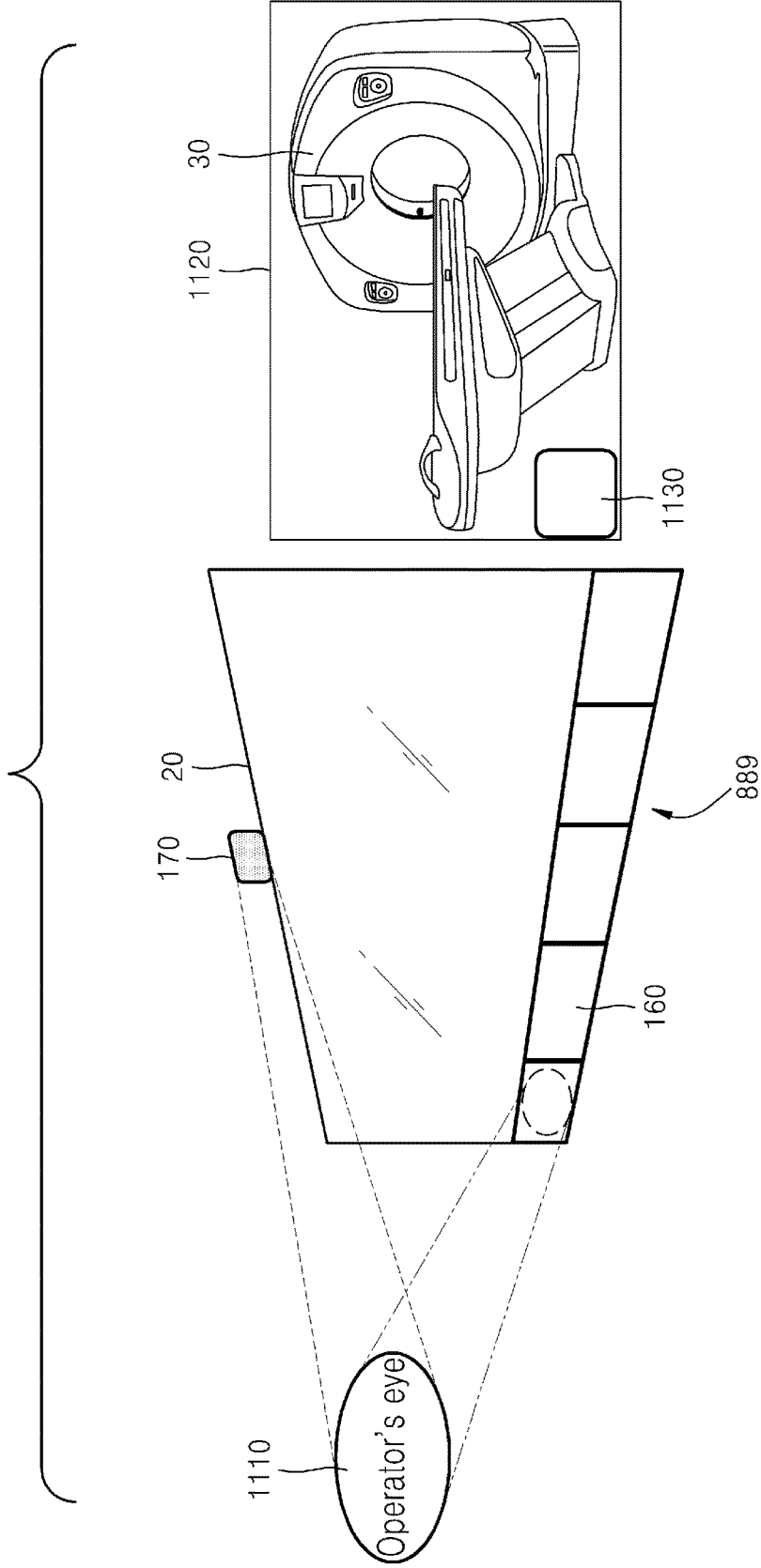
FIG. 11 illustrates a method of selecting a partial region of a room inside image according to an operator's view, according to an exemplary embodiment.

FIG. 11 illustrates a method of selecting, by the medical information providing apparatus 100, a partial region of a shield room inside image according to an operator's view, according to an exemplary embodiment.

In an exemplary embodiment of FIG. 11, the medical information providing apparatus 100 includes the displays 160 that are horizontally disposed at a lower end 889 of the console room window 20. The medical information providing apparatus 100 may also include the sensor 170 that is disposed at a top end of the console room window 20.

First, the medical information providing apparatus 100 captures an image of the inside of a shield room and then obtains a shield room inside image 1120. Afterward, the medical information providing apparatus 100 may detect an operator by using the sensor 170. In the present exemplary embodiment, the medical information providing apparatus 100 may recognize an operator's eye 1110 by using a view recognition sensor or an iris recognition sensor, and then may detect toward which display the operator's eye 1110 is directed.

The medical information providing apparatus 100 may select a partial region 1130 that is of the shield room inside image 1120 and that corresponds to a space of the shield room toward which the operator's eye 1110 is directed. Then, the medical information providing apparatus 100 provides an image of the partial region 1130 to the display 160. Accordingly, the medical information providing apparatus 100 may provide, to the display 160, the image of the inside of the shield room which matches the operator's eye 1110.

In the present exemplary embodiment, when a plurality of operators is in the console room, the medical information providing apparatus 100 may detect a specific operator. The medical information providing apparatus 100 may detect a view of the specific operator and may output the shield room inside image according to the view of the specific operator.

Figure 12:
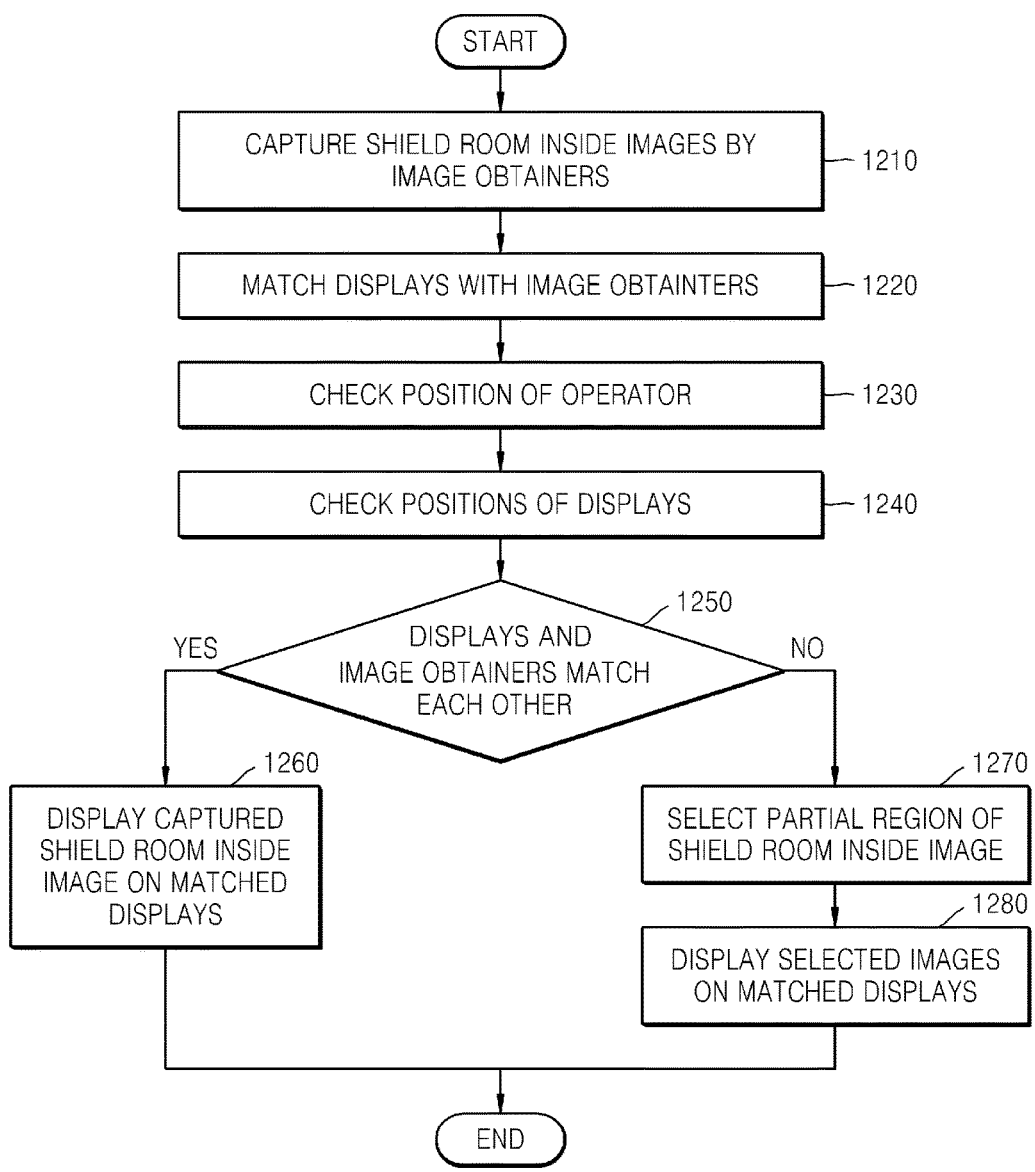
FIG. 12 is a flowchart of a method of capturing room inside images and outputting the room inside images to displays, according to an exemplary embodiment.

FIG. 12 is a flowchart of a method, performed by the medical information providing apparatus 100, of capturing shield room inside images by using a plurality of image obtainers, and outputting the shield room inside images to a plurality of displays, according to an exemplary embodiment.

In operation 1210, the medical information providing apparatus 100 captures the shield room inside images by using the plurality of image obtainers. The plurality of image obtainers will be described in detail with reference to FIG. 13.

In operation 1220, the medical information providing apparatus 100 matches the plurality of displays with the plurality of image obtainers. When the medical information providing apparatus 100 includes the same number of the plurality of displays and the plurality of image obtainers, the plurality of displays and the plurality of image obtainers may correspond to each other in a 1:1 manner.

On the other hand, the plurality of displays and the plurality of image obtainers may not match each other in the 1:1 manner. For example, two displays and one image obtainer may match each other, or vice versa.

According to the matching relation, the medical information providing apparatus 100 may provide a shield room inside image, which is captured by an image obtainer, to a display that corresponds to the image obtainer.

In operation 1230, the medical information providing apparatus 100 checks a position of an operator. In operation 1240, the medical information providing apparatus 100 checks positions of the plurality of displays.

In operation 1250, the medical information providing apparatus 100 determines whether the plurality of displays and the plurality of image obtainers match each other in the 1:1 manner. When the plurality of displays and the plurality of image obtainers match each other in the 1:1 manner, the medical information providing apparatus 100 proceeds to operation 1260, and if not, the medical information providing apparatus 100 proceeds to operation 1270.

According to the present exemplary embodiment, in operation 1250, the medical information providing apparatus 100 may determine the 1:1 matching relation by using the matching relation of operation 1220.

In operation 1260, the medical information providing apparatus 100 displays the shield room inside images, which are captured by the plurality of image obtainers in operation 1210, to the plurality of displays that are matched with the plurality of image obtainers.

In operation 1270, the medical information providing apparatus 100 selects a partial region of the shield room inside image. That is, when the plurality of displays and the plurality of image obtainers do not match each other in the 1:1 manner, the medical information providing apparatus 100 selects partial regions of the shield room inside images that are captured by the plurality of image obtainers, respectively.

That is, the medical information providing apparatus 100 may select the partial regions of the shield room inside image captured by the image obtainers and that are to be provided to the displays that are matched with the image obtainers, respectively. That is, the medical information providing apparatus 100 may determine images of regions to be displayed on the displays.

The medical information providing apparatus 100 may select the partial regions by using a plurality of pieces of information about the position of the operator and the positions of the displays which are obtained in operations 1230 and 1240. That is, as described above with reference to FIGS. 9 and 10, when the medical information providing apparatus 100 selects the partial regions, the medical information providing apparatus 100 may refer to the arrangement of the displays and a positional relation with the operator.

In operation 1280, the medical information providing apparatus 100 displays the selected images on the matched displays, respectively. The medical information providing apparatus 100 may divide the shield room inside image by referring to a matching relation between the image obtainers and the displays, and then may display the divided shield room inside images on the displays.

Figure 13A:
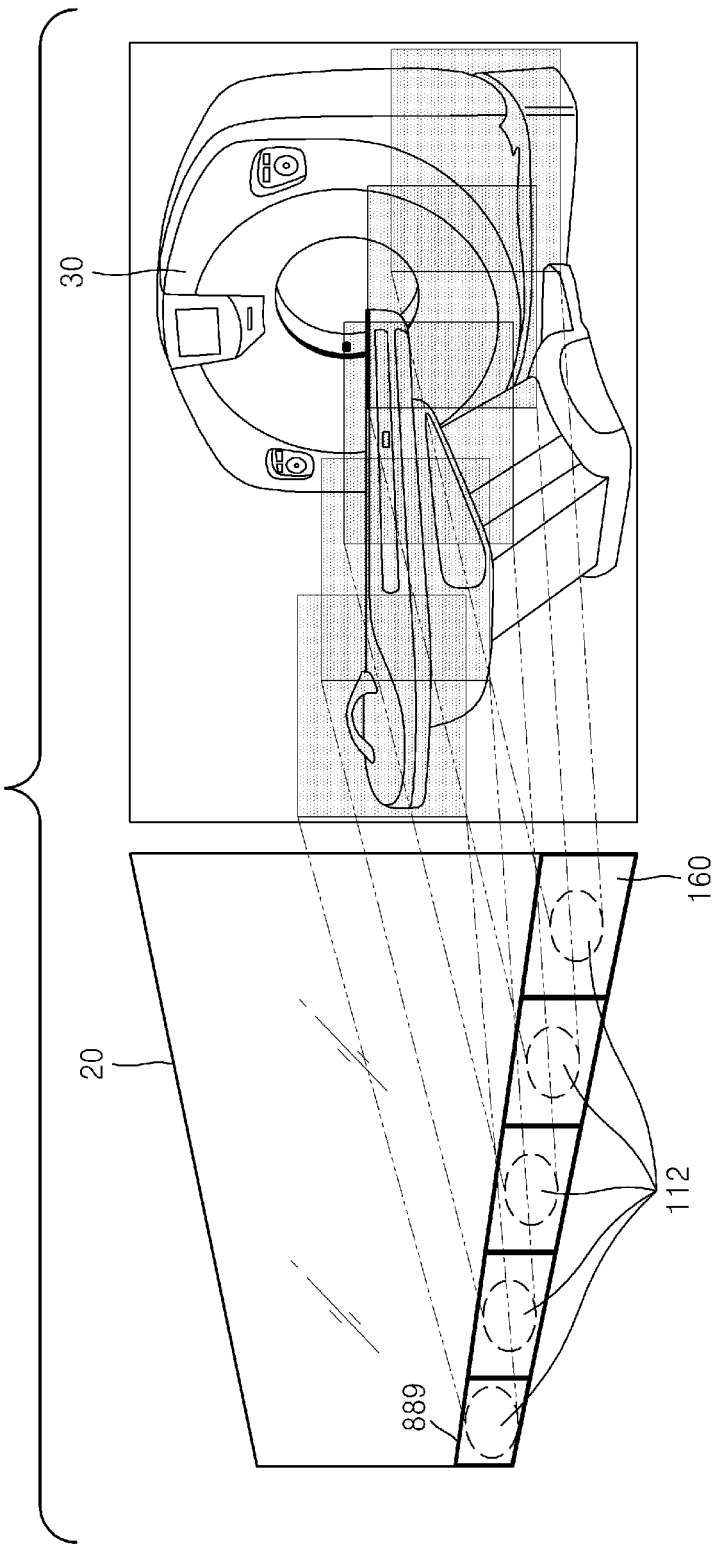
FIGS. 13A and 13B illustrate image obtainers capturing room inside images, according to exemplary embodiments.
Figure 13B:
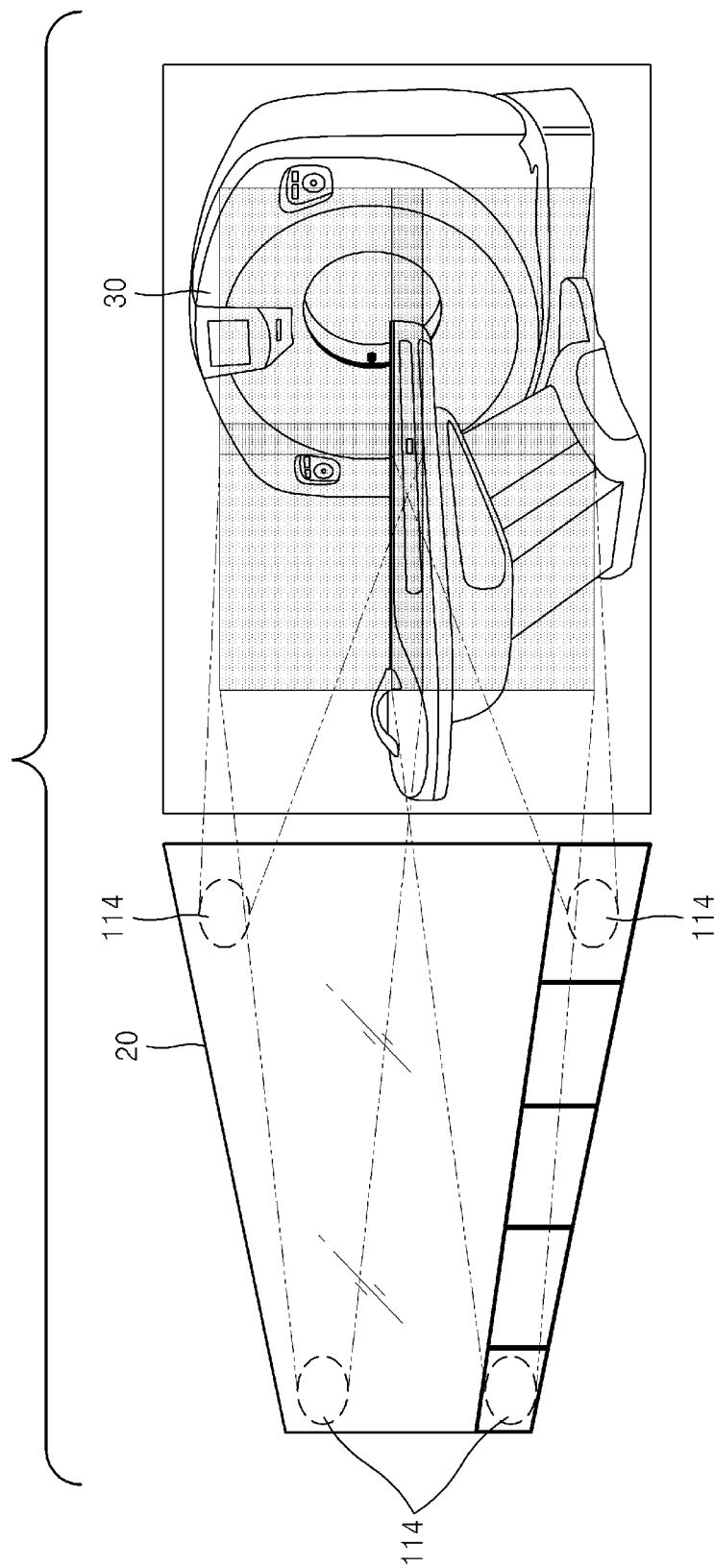

FIGS. 13A and 13B illustrate image obtainers 112 capturing shield room inside images, according to exemplary embodiments of the present invention.

In an exemplary embodiment of FIG. 13A, the image obtainers 112 and the displays 160 match each other in a 1:1 manner. In the present exemplary embodiment, the medical information providing apparatus 100 includes five image obtainers 112 and five displays 160. The displays 160 are disposed in one direction at a lower end 889 of the console room window 20. In the present exemplary embodiment, the image obtainers 112 may be disposed at back sides of the matched displays 160.

The image obtainers 112 capture shield room inside images, respectively, and the medical information providing apparatus 100 provides the shield room inside images to the matched displays 160. Since the image obtainers 112 and the displays 160 match each other in the 1:1 manner, the medical information providing apparatus 100 may directly provide the shield room inside images to the displays 160.

The image obtainer 112 may capture an image of an overlapping region in the shield room. That is, the image obtainers 112 may capture overlapping images of the shield room to capture an entire region inside the shield room.

Accordingly, the medical information providing apparatus 100 may select partial regions of the shield room inside images that are generated by the image obtainers 112 and may provide them to the displays 160. For example, the medical information providing apparatus 100 may select the partial regions of the shield room inside images, based on a position of a sensed operator, a distance between the operator and the display 160, a direction of a view of the operator, or the like.

In an exemplary embodiment of FIG. 13B, image obtainers 114 and the displays 160 do not match each other in a 1:1 manner. In the present exemplary embodiment, the medical information providing apparatus 100 includes five displays 160, and four image obtainers 114 that are disposed at four corners of the console room window 20.

Each of four image obtainers 114 captures a shield room inside image. Similar to FIG. 13A, four image obtainers 114 may capture overlapping images of a shield room to capture an entire region inside the shield room.

The medical information providing apparatus 100 may select partial regions of shield room inside images that are captured by the four image obtainers 114, and then may provide the partial regions to five displays 160. That is, the medical information providing apparatus 100 may select five partial regions of the shield room inside images captured by four image obtainers 114, and may provide images of five partial regions to the five displays 160, respectively, according to a matching relation.

Figure 14:
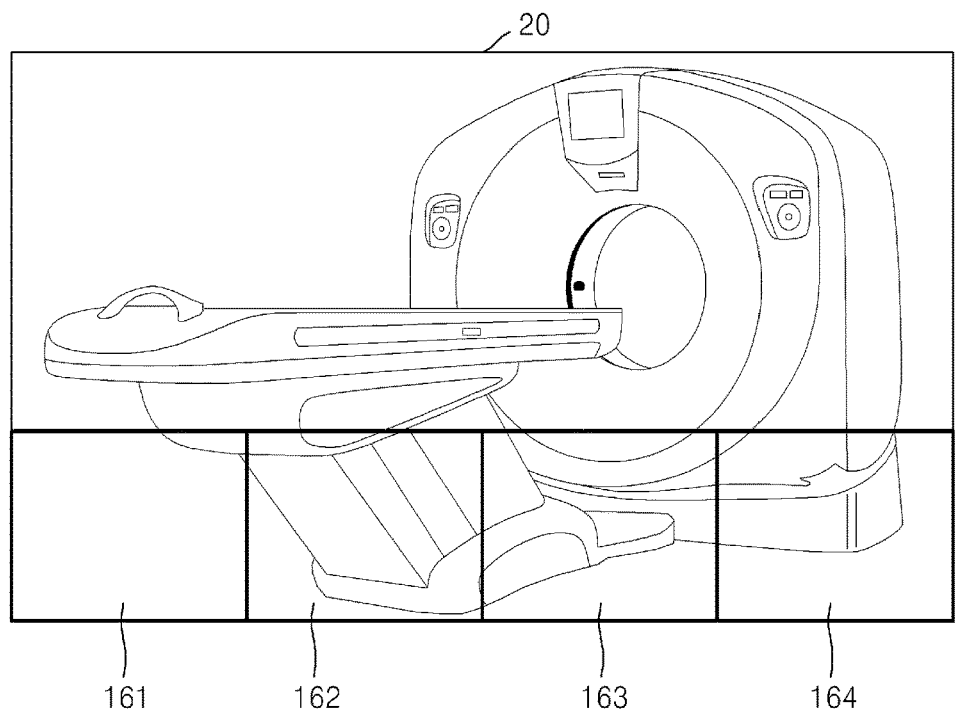
FIG. 14 illustrates an example in which the medical information providing apparatus outputs a room inside image to a plurality of displays, according to an exemplary embodiment.

FIG. 14 illustrates an example in which the medical information providing apparatus 100 outputs a shield room inside image to a plurality of displays, according to an exemplary embodiment.

In the present exemplary embodiment, the medical information providing apparatus 100 includes four the displays 160. The displays 160 are arrayed in one direction at a lower end of the console room window 20. However, a number and arrangement of the displays 160 are not limited to the exemplary embodiment of FIG. 14.

The medical information providing apparatus 100 determines a first mode for medical information providing modes of four displays 160, and outputs the shield room inside image.

The medical information providing apparatus 100 selects four partial regions from the shield room inside image, and provides images of the partial regions to the displays 160, respectively. The medical information providing apparatus 100 may select four partial regions to be spatially connected to each other.

As illustrated in FIG. 14, the partial regions of the shield room inside image which are output via a first display 161 and a second display 162 are spatially connected to each other. That is, the medical information providing apparatus 100 selects two partial regions that are sequentially connected to each other in the shield room inside image, and outputs images of the sequentially-connected two partial regions to the adjacent first and second displays 161 and 162.

Similarly, the partial regions of the shield room inside image which are output to the second display 162, a third display 163, and a fourth display 164 may be sequentially connected to each other. That is, the medical information providing apparatus 100 may provide images of the partial regions selected from the shield room inside image to the displays 160 that are matched with the partial regions, respectively.

As described above, when the medical information providing apparatus 100 outputs the shield room inside image to the display 160 that is in the first mode, the medical information providing apparatus 100 may consider a position of an operator, a distance between the operator and the display 160, or the like. The medical information providing apparatus 100 may select a partial region to be displayed on the display 160, in consideration of a direction of a view of the operator according to the position of the operator while the operator watches the inside of the shield room.

According to the present exemplary embodiment, the medical information providing apparatus 100 may allow a view of the operator who watches the inside of the shield room via the console room window 20 to be connected with a view of the operator who watches the shield room via the shield room inside image that is output to the display 160, so that the medical information providing apparatus 100 may provide an effect of enlarging the console room window 20 with respect to the operator. Also, the medical information providing apparatus 100 may output images that are connected between the displays 160. In exemplary embodiments including transparent displays, the first mode and the third mode may allow the operator to obtain a see through shield room inside view, for which in the first and third modes and at least partially transparent mode of the displays may be set. In the first display mode, in fact no display is achieved, other than to allow the see through effect.

Figure 15:
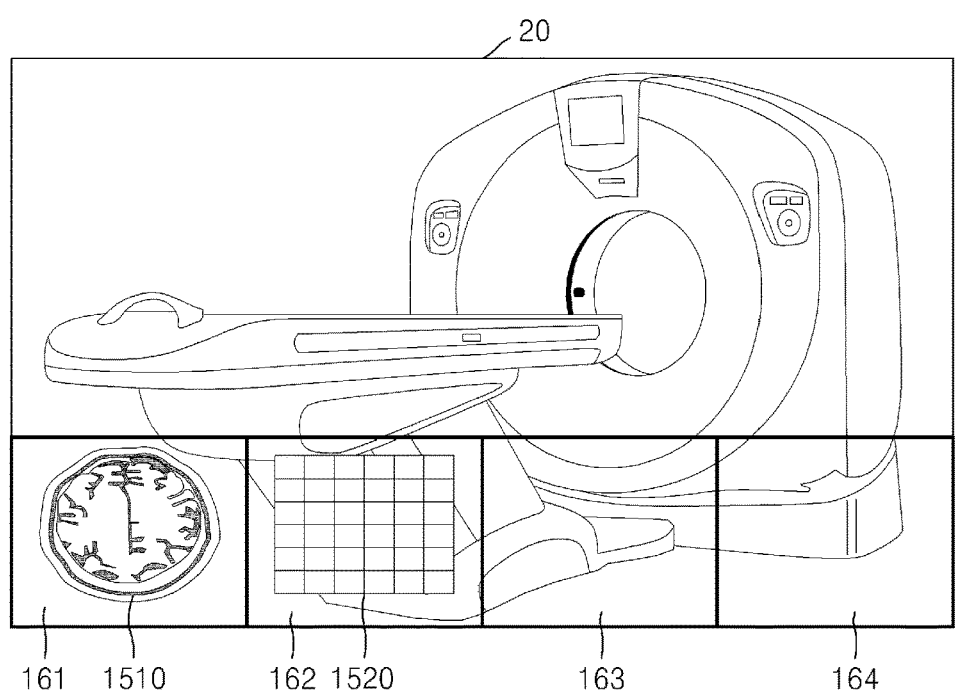
FIG. 15 illustrates an example in which the medical information providing apparatus provides medical information during a second mode or a third mode, according to an exemplary embodiment.

FIG. 15 illustrates an example in which the medical information providing apparatus 100 provides medical information in a second mode or a third mode, according to an exemplary embodiment.

In an exemplary embodiment of FIG. 15, the medical information providing apparatus 100 receives diagnostic information from the medical diagnostic system 30. That is, the medical information providing apparatus 100 may capture the shield room inside image according to a first mode, and also may receive the diagnostic information from the medical diagnostic system 30 or an external server.

In an exemplary embodiment of FIG. 15, the medical information providing apparatus 100 obtains a medical image 1510 and a medical image capturing schedule 1520 as the diagnostic information. That is, when a diagnostic imaging with respect to a head of an object is completed, the medical information providing apparatus 100 may obtain the medical image 1510 of the object from the medical diagnostic system 30 and may obtain the medical image capturing schedule 1520 including information about a next diagnostic target of the object. The medical image 1510 and the medical image capturing schedule 1520 are examples of the diagnostic information and are for convenience of description; thus, the diagnostic information is not limited thereto.

The medical information providing apparatus 100 may receive the diagnostic information and may determine the medical information providing mode of the display 160 as the second mode or the third mode. As described above, the second mode is the medical information providing mode in which the diagnostic information is provided, and the third mode is the medical information providing mode in which the diagnostic information and the shield room inside image are provided together.

In an exemplary embodiment of FIG. 15, the medical information providing apparatus 100 provides the medical image 1510 to the first display 161, and provides the medical image capturing schedule 1520 to the second display 162. An order of providing, by the medical information providing apparatus 100, the diagnostic information to the displays 160 will be described in detail with reference to FIGS. 17 through 19.

When the medical information providing apparatus 100 determines the medical information providing mode as the second mode or the third mode, the medical information providing apparatus 100 may determine a pre-set medical information providing mode according to a type of the diagnostic information. Alternatively, the medical information providing apparatus 100 receives a user input for selecting a medical information providing mode and may determine the medical information providing mode according to the user input.

For example, when a medical information providing mode with respect to the medical image 1510 is pre-set as the second mode, the medical information providing apparatus 100 may determine a medical information providing mode of a display for outputting medical information as the second mode. On the other hand, although a medical information providing mode with respect to the medical image capturing schedule 1520 is pre-set as the second mode, the medical information providing apparatus 100 may receive a user input command to overlay the medical image capturing schedule 1520 on the shield room inside image, and thus may output the medical image capturing schedule 1520 in the third mode on the second display 162.

In more detail with respect to the present exemplary embodiment, the medical information providing apparatus 100 provides the medical image 1510 to the first display 161 in the second mode. The medical information providing apparatus 100 provides the medical image capturing schedule 1520 to the second display 162 in the third mode. As illustrated, the second display 162 may overlay the medical image capturing schedule 1520 on the shield room inside image so that the second display 162 may provide two types of information together.

The medical information providing apparatus 100 may maintain the medical information providing mode that is the first mode for the third display 163 and the fourth display 164. However, when the medical information providing apparatus 100 obtains new diagnostic information from the medical diagnostic system 30 or receives a user input commanding to transfer the diagnostic information to another display 160, the medical information providing apparatus 100 may change the medical information providing mode of the third display 163 and/or the fourth display 164 into the second mode or the third mode. That is, the medical information providing apparatus 100 may additionally display the new diagnostic information on the third display 163 and/or the fourth display 164.

Figure 16:
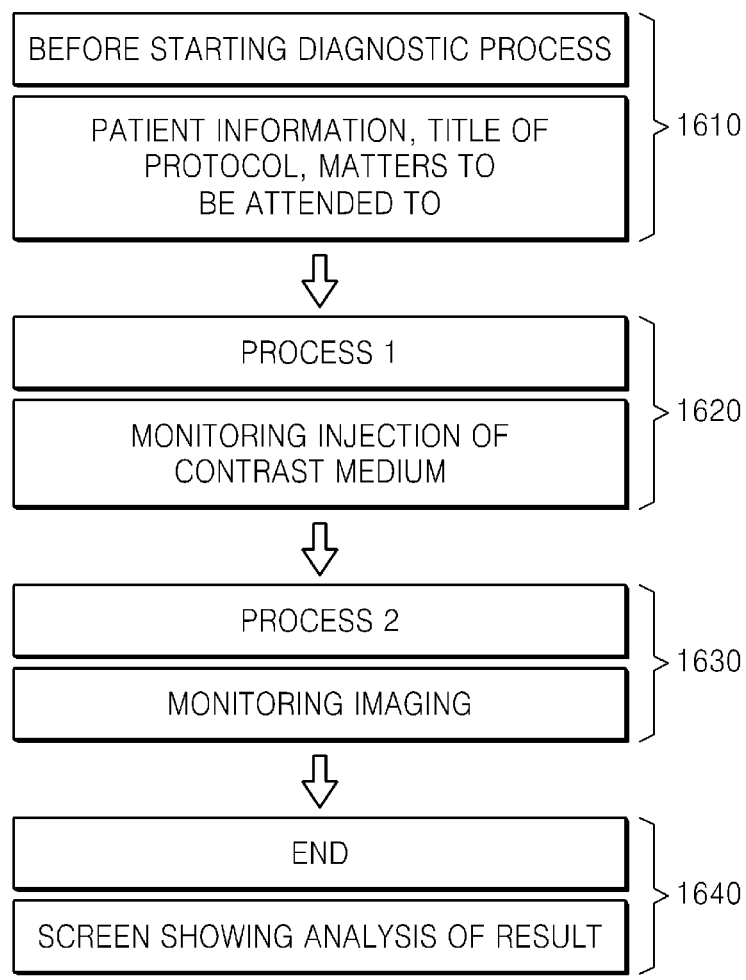
FIG. 16 illustrates a method of changing a medical information providing mode, according to an exemplary embodiment.

FIG. 16 illustrates a method of changing a medical information providing mode, by the medical information providing apparatus 100, when a diagnostic process with respect to an object is performed by the medical diagnostic system 30, according to an exemplary embodiment.

As described above with reference to FIGS. 14 and 15, the medical information providing apparatus 100 may include four displays 160 that are arrayed in one direction at a lower end of the console room window 20. Operation 1610 illustrates a situation before diagnostic imaging starts and the medical diagnostic system 30 generates general information such as patient information related to the object, a medical image capturing schedule, or the like that is used to image the object.

Accordingly, the medical information providing apparatus 100 may obtain, from the medical diagnostic system 30, diagnostic information including the patient information, ID information, information about a diagnostic target part, information about a title of an examination protocol, information about matters to be attended to when imaging a patient, or the like.

The medical information providing apparatus 100 may display the diagnostic information, which is obtained in operation 1610, on the display 160. For example, the medical information providing apparatus 100 may display the diagnostic information of operation 1610 on the first display 161.

Operation 1620 illustrates an ongoing diagnostic process. During the diagnostic process with respect to the object, the medical diagnostic system 30 may inject a contrast medium into the object.

In this regard, the medical information providing apparatus 100 may obtain diagnostic information including information about an injection amount of the contrast medium, an injection speed of the contrast medium, a path along which the contrast medium spreads, or the like. Also, the medical information providing apparatus 100 may display the diagnostic information, which is obtained in operation 1620, on the display 160. For example, the medical information providing apparatus 100 may display the diagnostic information of operation 1620 on the second display 162. In another exemplary embodiment, the medical information providing apparatus 100 may transfer the diagnostic information of operation 1610 from the first display 161 to the second display 162 and may display it on the second display 162, and may display the diagnostic information of operation 1620 on the first display 161.

Operation 1630 illustrates an ongoing diagnostic process after the contrast medium is injected. The medical diagnostic system 30 may generate a medical image obtained by capturing an image of the object by using the contrast medium.

Accordingly, the medical information providing apparatus 100 may obtain diagnostic information including a plurality of the medical images from the medical diagnostic system 30. That is, the medical information providing apparatus 100 may obtain the medical image that indicates a result of a protocol processed in the medical diagnostic system 30, and may display the medical image on the display 160.

In the present exemplary embodiment, the medical information providing apparatus 100 may display the medical image of operation 1630 on the third display 163 or the fourth display 164. On the other hand, the medical information providing apparatus 100 may display the medical image on the first display 161 or the second display 162, and may transfer the diagnostic information that has been displayed on the first display 161 or the second display 162 to another display and may display the diagnostic information on the other display.

Operation 1640 illustrates a situation in which the diagnostic is ended and, the medical diagnostic system 30 may output an analysis result about the diagnosis. For example, the medical diagnostic system 30 may calculate a size, a length, and a volume value of the diagnostic target part of the object, and may image a path of a blood vessel into which the contrast medium is injected. Also, the medical diagnostic system 30 may generate an image showing a position in the diagnostic target part which is estimated to have a tumor.

Accordingly, the medical information providing apparatus 100 may obtain diagnostic information including analysis information with respect to the diagnostic result. Also, the medical information providing apparatus 100 may obtain information about a next target part to be captured, and may also obtain information about a medical image capturing schedule. The medical information providing apparatus 100 may display the obtained information on one of four displays 160.

In the present exemplary embodiment, the medical information providing apparatus 100 may obtain a plurality of pieces of diagnostic information as the diagnostic processes with respect to the object proceed, and may determine the medical information providing mode of the display 160. Also, the medical information providing apparatus 100 may determine the medical information providing mode of the display 160 as a number of pieces of the diagnostic information obtained from the medical diagnostic system 30 is increased according to new diagnostic information.

The medical information providing apparatus 100 may determine the medical information providing modes of the displays 160, and may provide a plurality of pieces of diagnostic information, which are different from each other, to the displays 160, respectively.

Figure 17:
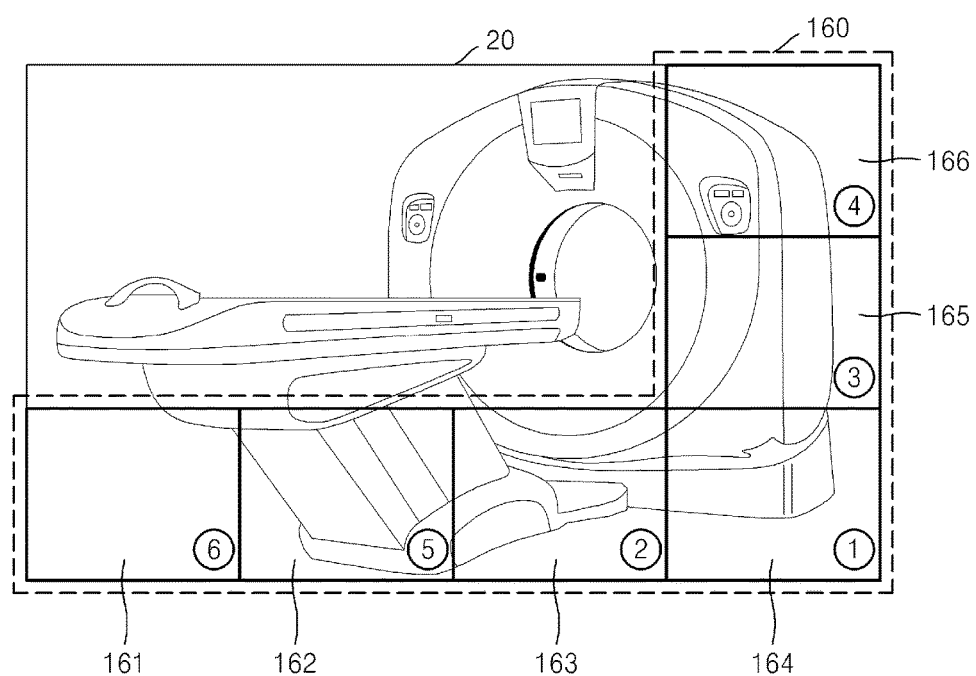
FIG. 17 illustrates priority orders that are set in the displays, according to an exemplary embodiment.

FIG. 17 illustrates priority orders that are set in the displays 160 included in the medical information providing apparatus 100, according to an exemplary embodiment.

The medical information providing apparatus 100 may set the priority orders in the displays 160. The priority orders may mean orders among the displays 160, and the medical information providing apparatus 100 may provide a plurality of pieces of obtained diagnostic information to the displays 160 according to the orders.

The medical information providing apparatus 100 may determine the priority orders in the displays 160, based on various criteria. For example, the medical information providing apparatus 100 may determine the priority orders by referring to a positional relation between the console room window 20 and the displays 160, such as an arrangement of the displays 160, positions of the displays 160, or the like, and/or by referring to specifications such as a size, resolution, or the like of the displays 160.

Six displays 160 shown in FIG. 17 may have the priority orders that correspond to the depicted numbers from 1 to 6.

In more detail with respect to the present exemplary embodiment, the medical information providing apparatus 100 of FIG. 17 may obtain diagnostic information from the medical diagnostic system 30 and may output the diagnostic information to the fourth display 164 (with the number "1") having the highest priority order and positioned at a lower right corner.

Then, the medical information providing apparatus 100 may further obtain two types of diagnostic information and may provide the two types of diagnostic information to the third and fifth displays 163 and 165 (with the numbers "2" and "3") having the next-highest priority order. That is, the priority orders set in the displays 160 may mean an order by which the medical information providing apparatus 100 displays diagnostic information on the displays 160.

In another exemplary embodiment, the medical information providing apparatus 100 may set the same priority order in two or more displays 160. For example, the first, second, and sixth displays 161, 162, 166 with the numbers "4", "5", and "6" may have the same priority order.

In the present exemplary embodiment, when the medical information providing apparatus 100 outputs diagnostic information, the medical information providing apparatus 100 may consider the priority orders and also may consider a position of an operator or a direction of a view of the operator. That is, if three displays 160 have the same priority order, the medical information providing apparatus 100 may determine one of three displays 160 to display diagnostic information that is obtained by detecting an operator. For example, when the user is positioned in a right side of the console room window 20, the medical information providing apparatus 100 may display the diagnostic information on the sixth display 166 having the number "4" that is adjacent to the operator.

FIG. 18 illustrates an example in which the medical information providing apparatus 100 outputs diagnostic information according to priority orders of displays, according to an exemplary embodiment.

As illustrated in FIG. 17, the medical information providing apparatus 100 may set the priority orders of the six displays. In an exemplary embodiment of FIG. 18, different priority orders are set in the six displays, but, as described above, the same priority order may be set in two or more displays.

Referring to an upper diagram of FIG. 18, the medical information providing apparatus 100 obtains, from the medical diagnostic system 30, diagnostic information that is a brain medical image about a brain. The medical information providing apparatus 100 may output the brain medical image, which is the obtained diagnostic information, to a display 1810 with a number "1" having the highest priority order.

Afterward, referring to a lower diagram of FIG. 18, the medical information providing apparatus 100 obtains, from the medical diagnostic system 30, another medical image as diagnostic information that is an abdomen medical image. The medical information providing apparatus 100 may output the abdomen medical image to a display 1820 with a number "2" having the second-highest priority order.

Although not illustrated, when the medical information providing apparatus 100 additionally obtains third diagnostic information from the medical diagnostic system 30, the medical information providing apparatus 100 may display the third diagnostic information on a display 1822 with a number "3".

FIG. 19 illustrates an example in which the medical information providing apparatus 100 outputs diagnostic information to displays according to importance of the diagnostic information, according to an exemplary embodiment. In an exemplary embodiment of FIG. 19, the medical information providing apparatus 100 may set priority orders in six displays, wherein the priority orders are the same as the priority orders described with reference to FIG. 17.

Referring to an upper diagram of FIG. 19, the medical information providing apparatus 100 obtains a medical image capturing schedule as diagnostic information from the medical diagnostic system 30. The medical information providing apparatus 100 may change a medical information providing mode of a display 1910 having the highest priority order and positioned in a lower right corner from a first mode to a second mode or a third mode. Afterward, the medical information providing apparatus 100 may output the diagnostic information that is the medical image capturing schedule to the display 1910 having the changed medical information providing mode.

Referring to a lower diagram of FIG. 19, the medical information providing apparatus 100 obtains a brain medical image as new diagnostic information. Although the priority orders are set in six displays, the medical information providing apparatus 100 may provide information according to importance of the diagnostic information, rather than according to the priority orders of the displays. Alternatively, the priority order may be set depending on the time on which the diagnostic information has become available for display, and the highest priority displays 1910 is then made available to present the newest diagnostic information.

In more detail, the importance of diagnostic information including a medical image capturing schedule may be lower than the importance of a medical image. That is, the medical information providing apparatus 100 may output diagnostic information to a display, in consideration of importance that is pre-set according to a type of the diagnostic information.

In the present exemplary embodiment, the medical information providing apparatus 100 may display the medical image, which is diagnostic information having higher importance, to the display 1910 having the highest priority order and positioned in the lower right corner. The medical information providing apparatus 100 may transfer and then may display the diagnostic information including the medical image capturing schedule to a display 1920 having the second-highest priority order.

That is, when the medical information providing apparatus 100 obtains more pieces of diagnostic information, the medical information providing apparatus 100 may output diagnostic information in consideration of both priority orders of the displays and importance of the diagnostic information.

Although not illustrated, when the medical information providing apparatus 100 obtains diagnostic information having importance higher than the medical image, the medical information providing apparatus 100 may transfer and then may output the diagnostic information including the medical image capturing schedule and the medical image to a display having a priority order lower than the display that has output the diagnostic information including the medical image capturing schedule and the medical image.

Figure 20:
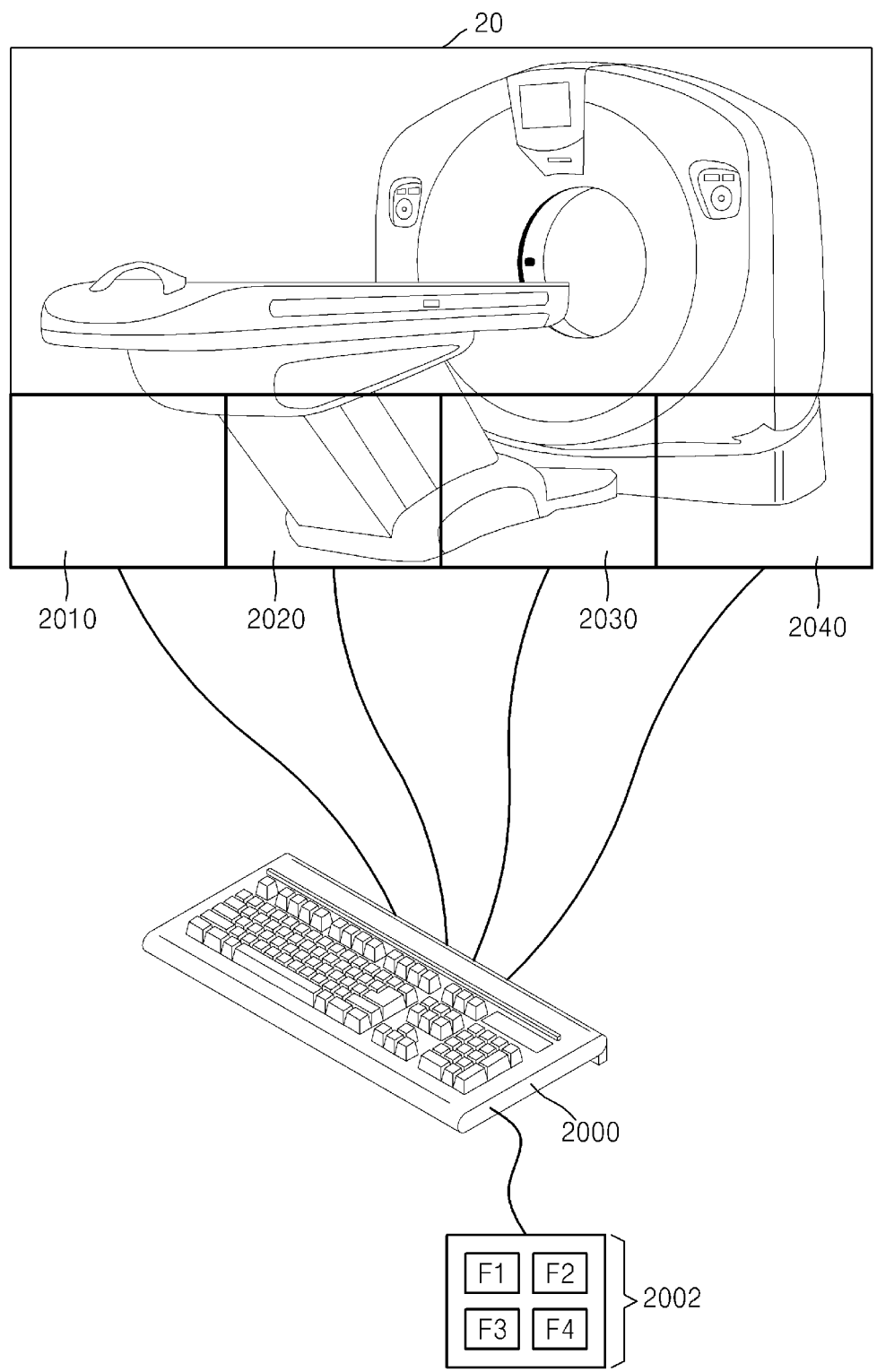
FIG. 20 illustrates a user input unit that commonly corresponds to a plurality of displays, according to an exemplary embodiment.

FIG. 20 illustrates a user input unit that commonly corresponds to a plurality of displays, according to an exemplary embodiment.

In an exemplary embodiment of FIG. 20, the medical information providing apparatus 100 includes four displays (i.e., the first, second, third and fourth displays 2010, 2020, 2030, and 2040) and a user input unit 2000 that commonly corresponds to four displays, but the number of displays is not limited to four. For example, the medical information providing apparatus 100 may include 1, 2, 3, 5, 6, . . . 10, . . . 20, etc. displays.

As described above with reference to FIG. 1, a plurality of user input units is positioned in the console room to control the medical diagnostic system 30. When the medical information providing apparatus 100 separately includes a plurality of user input units with respect to a plurality of displays, manipulation convenience may deteriorate and such a configuration may be spatially inefficient and economically deficient.

Accordingly, the medical information providing apparatus 100 shown in FIG. 20 may include the user input unit 2000 that corresponds to all of four displays. The medical information providing apparatus 100 receives a selection input with respect to selecting one of four displays via the user input unit 2000. Afterward, the medical information providing apparatus 100 may receive a control input with respect to controlling the selected display, via the user input unit 2000.

For example, the medical information providing apparatus 100 receives a selection input by which an operator selects the first display 2010. Afterward, the medical information providing apparatus 100 may receive, from the operator, a control input to control a shield room inside image or diagnostic information which is output to the first display 2010, and may control the first display 2010 according to the control input.

The medical information providing apparatus 100 may additionally receive a selection input by which the operator selects the third display 2030. When the medical information providing apparatus 100 receives the selection input and a control input with respect to the third display 2030, the medical information providing apparatus 100 may control the third display 2030.

The medical information providing apparatus 100 may receive an input as the selection input, wherein the input is generated by pressing a specific key of the user input unit 2000. For example, the medical information providing apparatus 100 may receive user inputs, which are generated by pressing function keys 2002 designated as F1, F2, F3, and F4, as selection inputs that select the first display 2010, the second display 2020, the third display 2030, and the fourth display 2040, respectively.

In the present exemplary embodiment, after the operator presses the function key F2, when the operator presses another key of the user input unit 2000, the medical information providing apparatus 100 may detect the second input by the operator as a control input with respect to the second display 2020.

FIGS. 21A, 21B, 21C, and 21D illustrate arrangements of a plurality of displays that are disposed adjacent to the console room window 20, according to an exemplary embodiment.

Figure 21A:
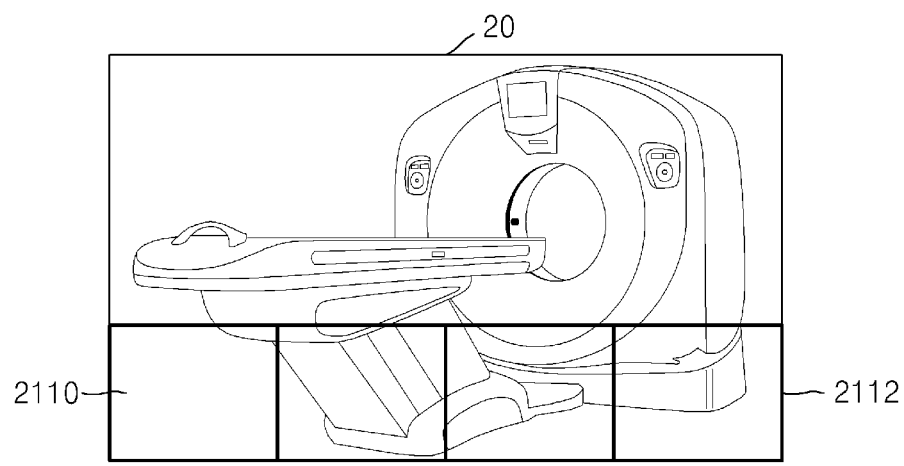
FIGS. 21A, 21B, 21C, and 21D illustrate exemplary display arrangements.

In an exemplary embodiment of FIG. 21A, the medical information providing apparatus 100 may include four displays 2110 that are disposed adjacent to a lower end of the console room window 20, on a display panel 2112.

Figure 21B:
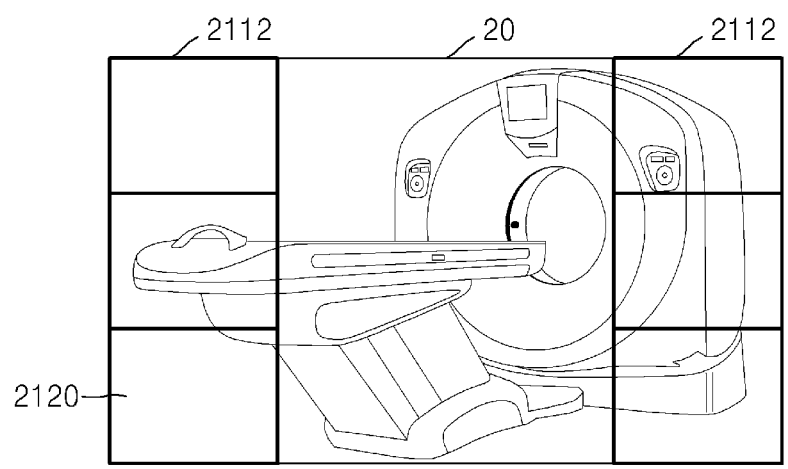

In an exemplary embodiment of FIG. 21B, the medical information providing apparatus 100 may include six displays 2120 that are disposed adjacent to left and right ends of the console room window 20, on the display panel 2112 including two portions which may be separated or may be formed as one integral structure.

Figure 21C:
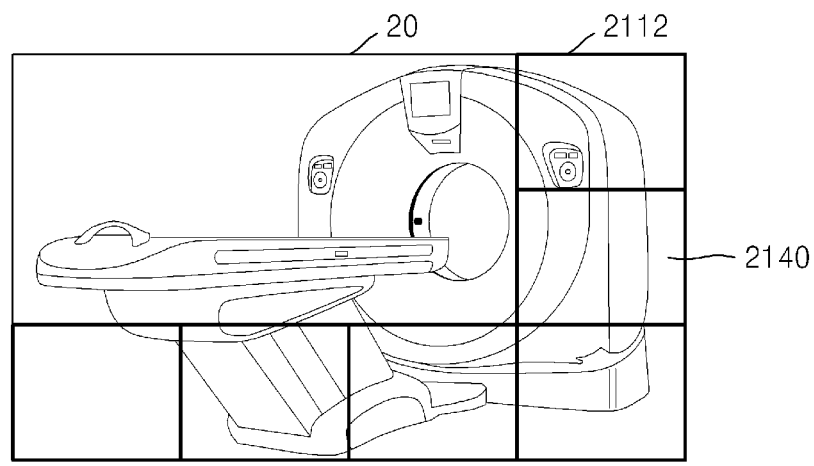

In an exemplary embodiment of FIG. 21C, the medical information providing apparatus 100 may include six displays 2140 that form an "L" shape-arrangement and are disposed adjacent to the console room window 20, on the display panel 2112.

Figure 21D:
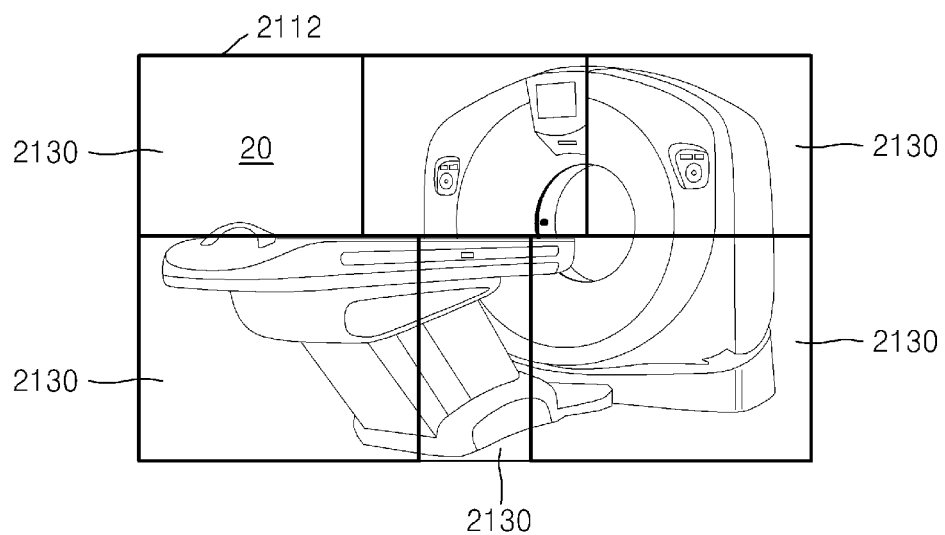

In an exemplary embodiment of FIG. 21D, the medical information providing apparatus 100 may include six displays 2130 that are disposed adjacent to the console room window 20, on the display panel 2112. The medical information providing apparatus 100 may include a plurality of displays having different sizes or equal sizes entirely covering the console room window 20 or leaving a small portion of the console room window 20 uncovered. The entire console window 20 may be covered by a single display which may be virtually divided into virtual displays of different size or of equal size, each providing medical or diagnostic information on a separate virtual display as described above.

The exemplary embodiments shown in FIGS. 21A to 21D are related to the medical information providing apparatus 100 including the plurality of displays. However, a number of the displays, the arrangements of the displays, and positions of the displays are not limited to the exemplary embodiments of FIGS. 21A to FIG. 21D.

Figure 22:
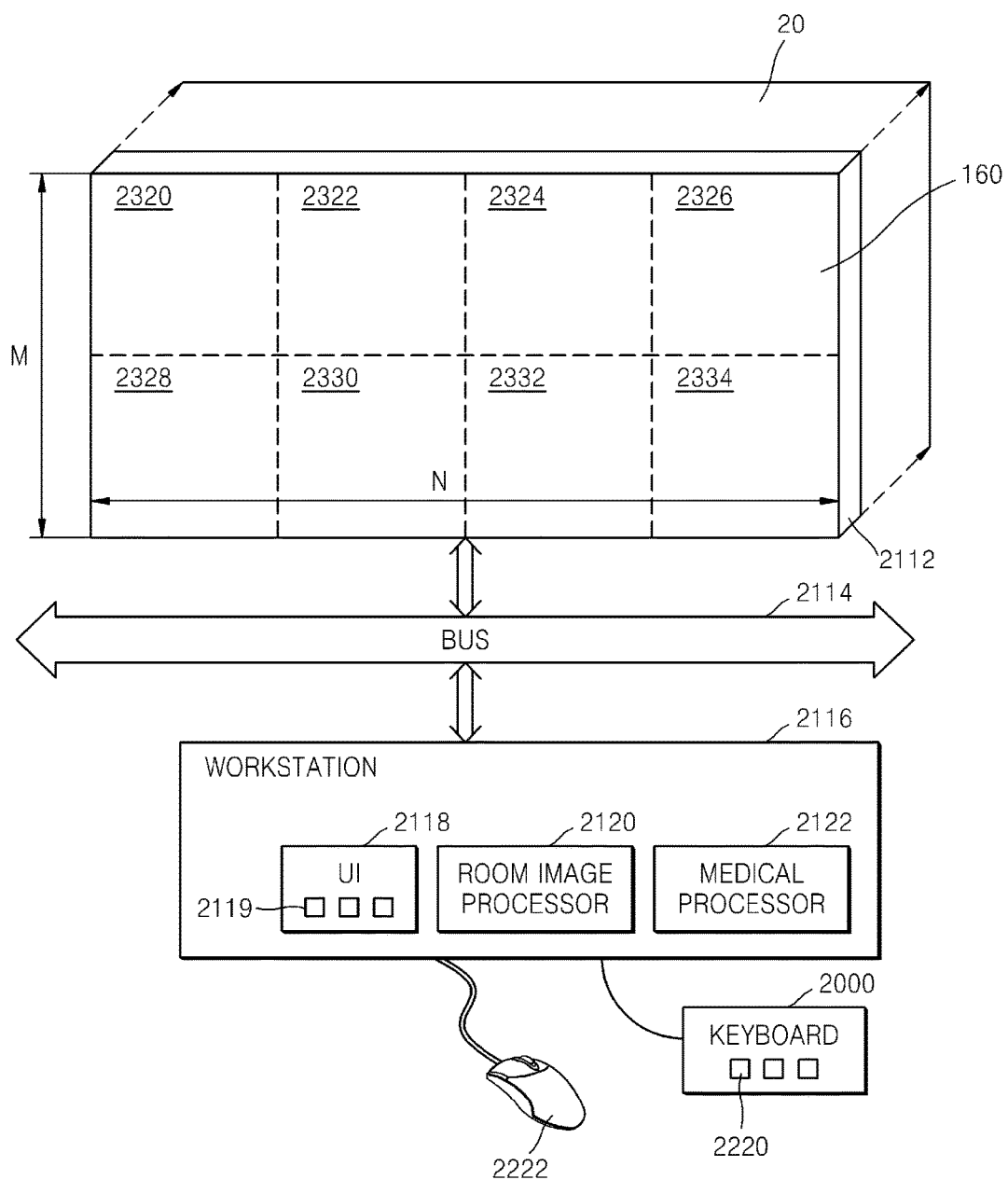
FIG. 22 illustrates a medical information providing system, according to an exemplary embodiment.

With reference to FIG. 22, the display panel 2112 may be a separate structure in the console room, may be attached to the console window 20, or may be incorporated in the console window 20. For example, the displays 160 may be formed as an integral structure with the console window 20 or may be fixed to the console window 20 by using adhesives, fixing members such as screws, etc. The structure including the console window 20 and the displays may then be installed between the examination room and the console room. As another example, the displays may be fixed to the console window 20 which is already installed between the examination room and the console room.

The displays 160 may be arranged in a M×N array and each display or a group of displays may be individually addressed, via a bus 2114, network, or other appropriate wired or wireless connections, by a user operating a workstation 2116. The workstation 2116 may include at least one of a user interface (UI) 2118, a keyboard 2000 including keys 2220, mouse 2222, etc. The UI 2118 may display various graphical objects 2119, menus, screens, etc., so that the user may control the medical examination of the object and the medical equipment disposed in the examination room and also may control the displays 160.

For example, the user may control the movement of the bed on which the object is disposed, the contrast injection apparatus to inject contrast into the object, a CT scanner and/or MRI system to perform the imaging of the object in the prescribed manner, etc.

For example, the user may control the displays 160 to define the medical information providing mode, set the priority order, enlarge or reduce the displayed image, move the image from one display to another, etc., by using the UI 2118, the keyboard 2000, the mouse 2222, etc.

For example, the UI 2118 may allow the operator to directly communicate with another professional, i.e., primary care physician, surgeon, etc. For example, when it is noted that an object may need additional diagnostic procedure to be executed, i.e., to image additional target area, to inject a different contrast, to perform a different MR sequence, etc., the operator may directly consult with another medical professional in charge of the object via the UI 2118 and may expeditiously receive the authorization for any further medical procedures for the object.

The workstation 2116 may include a room image processor 2180 configured to obtain the room image from the image obtainers and form a visual representation of the room image and a medical processor 2122 configured to process medical imaging information of the object and form a medical image of a region of interest (ROI) of the object.

Figure 23:
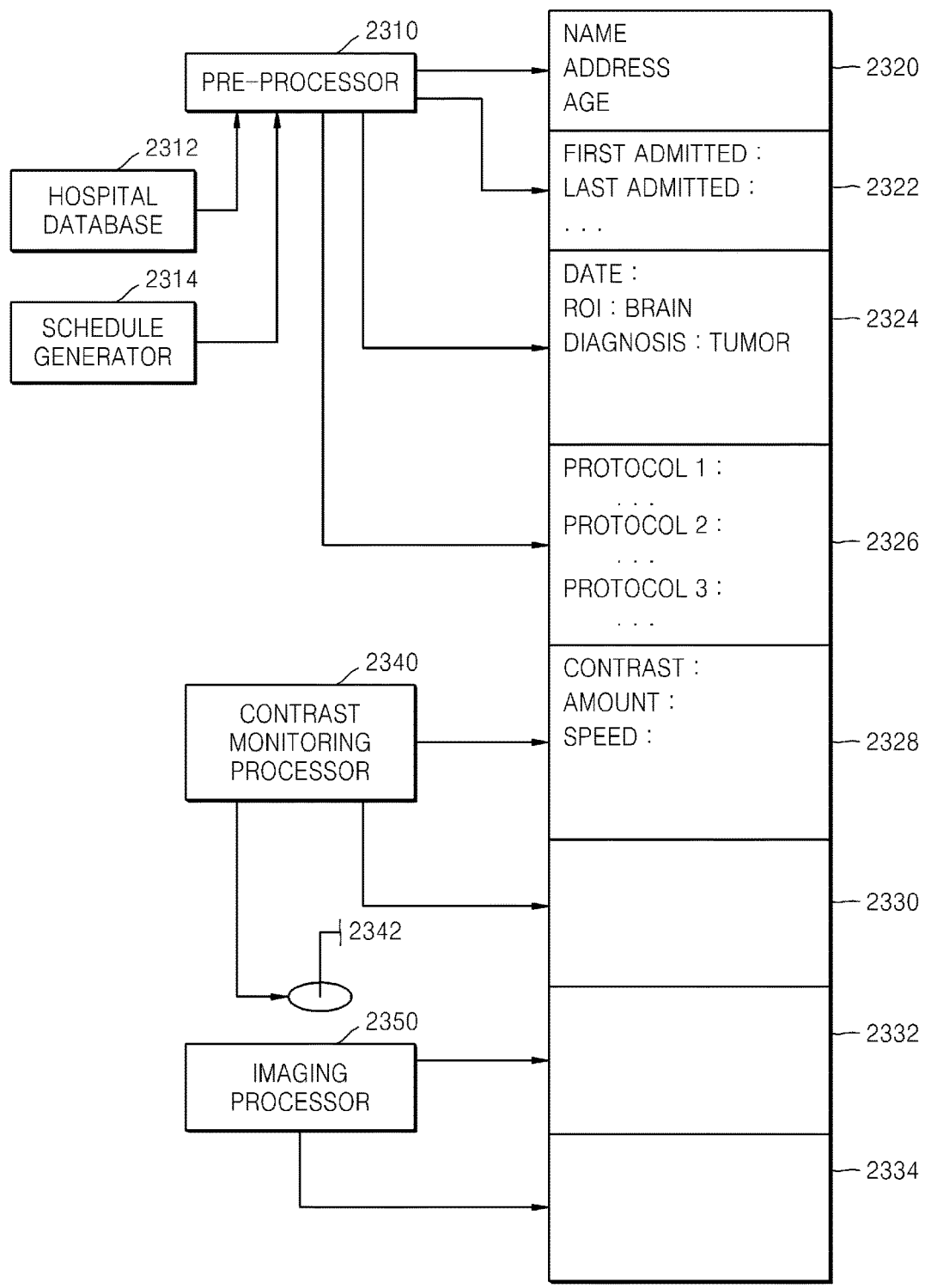
FIG. 23 illustrates a detail of a medical information providing system, according to an exemplary embodiment.
Figure 24:
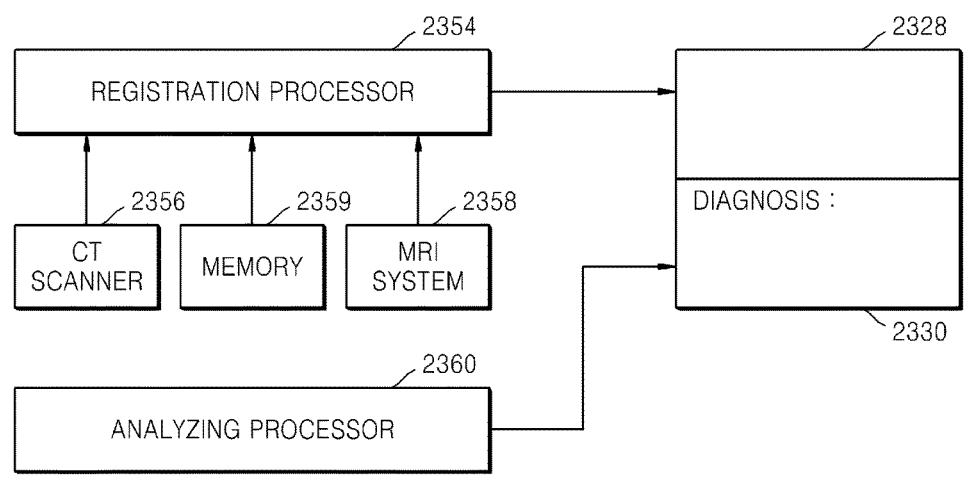
FIG. 24 illustrates a detail of a medical information providing system, according to an exemplary embodiment.

With reference to FIGS. 23 and 24, the medical processor 2122 may include a processor or processors which individually address each of the displays 160, each of the virtual displays, or groups of the displays or virtual displays.

For example, a pre-processor 2310 may be connected to the hospital database 2312 and may obtain preliminary medical information of the object, as for example, personal records, medical history records, results of the previous imaging procedures, etc., from the hospital database 2312. The pre-processor 2310 may also be connected to a schedule generator 2314 which generates an imaging schedule and/or imaging protocol for the imaging procedure, etc.

The pre-processor 2310 may display each piece of obtained medical information on a separate display or on the same display. For example, the pre-processor may display the personal records of the object on a first display 2320, the medical history records on a second display 2322, the results of the previous imaging procedure on a third display 2324, and an imaging protocol for the current imaging procedure on a fourth display 2326, etc.

The medical information may be displayed in the second medical information providing mode or the third medical information providing mode, while a fifth display 2328, a sixth display 2330, a seventh display 2332, and an eighth display 2334 may display the image of the examination room. The order of the display of the medical information may be defined for each display, as described above.

For example, the operation with respect to the pre-processor may correspond to the operation 1610, described above with reference to FIG. 16.

A contrast monitoring processor 2340 may control contrast injection equipment 2342 disposed in the examination room, to inject a contrast medium into the object. For example, the contrast monitoring processor 2340 may obtain and display a contrast name, an injection amount, an injection speed, and a predicted path along which the contrast medium would spread on the fifth display 2328. The contrast monitoring processor 2340 may monitor a path along which the contrast is spreading in the object and display a medical image of the spread of the contrast, on the sixth display 2330.

The medical information may be displayed in the second medical information providing mode or the third medical information providing mode, while the seventh display 2332 and the eighth display 2334 may display the image of the examination room. The order of the display of the medical information may be defined for each display. For example, the sixth display 2330, the seventh display 2332 and the eighth display 2334 may show images of the spread of the contrast at different time points.

For example, the operation with respect to the contrast monitoring processor may correspond to the operation 1620, described above with reference to FIG. 16.

An imaging processor 2350 may obtain and display a medical image of a region of interest (ROI) of the object captured by the imaging apparatus based on the executed imaging protocol, for example, an image of a brain, on the seventh display 2332, in the second medical information providing mode or the third medical information providing mode, while the eighth display 2334 may display the image of the examination room. The imaging processor 2350 may obtain and display another medical image of another ROI of the object captured by the imaging apparatus based on the executed imaging protocol, for example, an abdomen, on the eighth display 2334, in the second medical information providing mode or the third medical information providing mode.

A registration processor 2354 may obtain images of different modalities, for example, from the CT scanner 2356 and the MRI system 2358. Optionally, one of the images may be obtained from a memory 2359. Registration processor 2354 may register the images with one another and display superimposed image on one of the displays in the second medical information providing mode or the third medical information providing mode. For example, some of the previously displayed pieces of medical information, for example, the contrast related information and/or a contrast spreading image may be replaced with the superimposed image of different modalities.

For example, the operations of the imaging processor and the registration processor may correspond to operation 1630 described above with reference to FIG. 16.

An analyzing processor 2360 may analyze the medical information generated during the imaging of the patient and may output a diagnostic result of an analysis in the second medical information providing mode or the third medical information providing mode. For example, the analyzing processor 2360 may generate an image showing a position in the object which is estimated to have a tumor.

For example, the operation described above with respect to the analyzing processor may correspond to the operation 1640, described above with reference to FIG. 16.

As described above, the order of the display of the information may be defined for each display and may be set in the displays or determined by a user. The order of the displaying information described above is illustrative only and is not limiting. The displays of FIGS. 23 and 24 are illustrated as being arranged in a column, for convenience of the description and this is not limiting.

The exemplary embodiments may be written as computer programs and may be implemented in general-use computers that execute the programs using a computer-readable recording medium. Data structures used in exemplary embodiments may be written in a computer-readable recording medium through various means. Examples of the computer-readable recording medium include magnetic storage media (e.g., ROM, floppy disks, hard disks, etc.), optical recording media (e.g., CD-ROMs, or DVDs), etc.

It is for instance possible that console room window is formed as displays, wherein the display unit placed adjacent to the console room window form the enlarged observation area of the inside of the shield room.

The displays may further include a transparent or translucent display unit arranged be to be at least partially transparent or translucent, for instance in a display mode wherein no diagnostic information (including scan images and/or patient data and the like) is provided to (a part of) the display unit. Providing the shield room inside view to such a display unit, for instance in the first or third mode, may then include forming the display unit to be at least partially transparent. The display units may be provided on the control room window, i.e. within the boundaries of the control room window, as depicted for example in FIG. 21. In this exemplary embodiment, an image obtaining unit for capturing a shield room inside image may be omitted.

The described-above exemplary embodiments and advantages are merely exemplary and are not to be construed as limiting. The present teaching can be readily applied to other types of apparatuses. The description of exemplary embodiments is intended to be illustrative, and not to limit the scope of the claims, and many alternatives, modifications, and variations will be apparent to those skilled in the art.

What is claimed is:

1. A medical information providing method for providing medical information via a medical information providing apparatus, wherein the medical information providing apparatus comprises a plurality of displays disposed on a border with a console room window disposed between an examination room and a console room, and at least one image capturing device, the medical information providing method comprising:

capturing a room image of an inside of the examination room in which an object is positioned for medical examination by the at least one image capturing device;

obtaining information of at least one among a position of a user, a distance between the user and each of the plurality of displays, respectively, and a direction of a view of the user;

selecting, for each of the plurality of displays, a partial region of the captured room image a border of which is matched to a border of a room view observable via the console room window and to an image displayed on at least one display among the plurality of displays, based on the at least one among the position of the user, the distance between the user and each of the plurality of displays, respectively, and the direction of the view of the user, and displaying the selected partial region of the captured room image, on each of the plurality of displays, respectively.

2. The medical information providing method of claim 1, further comprising:

defining a medical information providing mode to include at least one selected from a first mode configured to provide diagnostic information to be overlaid on the selected partial region of the captured room image, a second mode configured to provide the selected partial region of the captured room image, and a third mode configured to provide the diagnostic information; and displaying at least one selected from the selected partial region of the captured room image and the diagnostic information according to the medical information providing mode, on the plurality of displays.

3. The medical information providing method of claim 2, wherein the displaying the at least one selected from the selected partial region of the captured room image and the diagnostic information comprises determining the medical information providing mode while a diagnostic process with respect to the object is being performed.

4. The medical information providing method of claim 3, wherein the displaying comprises:

displaying the room image according to the second mode on the at least one display;

changing the second mode of the plurality of displays to the third mode or the first mode, in response to starting the diagnostic process with respect to the object; and displaying the diagnostic information in the third mode or the first mode on the plurality of displays, in response to the changing.

5. The medical information providing method of claim 2, wherein the displaying the at least one selected from the selected partial region of the captured room image and the diagnostic information comprises determining the medical information providing mode of the plurality of displays.

6. The medical information providing method of claim 5, wherein the determining the medical information providing mode comprises determining the medical information providing mode of the plurality of displays as the third mode or the first mode, in response to starting a diagnostic process of the object.

7. The medical information providing method of claim 5, wherein the determining the medical information providing mode comprises changing the medical information providing mode of the plurality of displays, based on priority orders pre-set in the plurality of displays, respectively.

8. The medical information providing method of claim 7, wherein the priority orders are determined based on at least one among a position, a size, and a resolution of the plurality of displays, respectively.

9. The medical information providing method of claim 7, wherein the plurality of displays comprises a first display and a second display, and the displaying the at least one selected from the selected partial region of the captured room image and the diagnostic information further comprises:

displaying a first piece of the diagnostic information on the first display, in response to starting a diagnostic process of the object;

consequently, displaying the first piece of the diagnostic information on the second display having a lower priority than that of the first display, in response to the diagnostic process of the object being progressed and a second piece of the diagnostic information being obtained; and displaying the second piece of the diagnostic information on the first display in response to obtaining the second piece of the diagnostic information.

10. The medical information providing method of claim 5, wherein the plurality of displays is embodied in the console room window, and the plurality of displays is disposed adjacent each other along a side edge of the console room window or on an entirety of the console room window.

11. The medical information providing method of claim 5, wherein the displaying further comprises:

selecting a plurality of partial regions from the captured room image according to an arrangement of the plurality of displays;

matching the plurality of partial regions with the plurality of displays, respectively; and displaying images of the plurality of partial regions on the matched plurality of displays.

12. The medical information providing method of claim 11, wherein the plurality of partial regions are spatially connected to each other.

13. The medical information providing method of claim 5, further comprising:

receiving an external input signal via a user input unit that commonly corresponds to the plurality of displays; and controlling the plurality of displays based on the external input signal.

14. The medical information providing method of claim 1, wherein the selecting comprises selecting the partial region based on an identification (ID) device configured to identify an operator.

15. The medical information providing method of claim 14, wherein the selecting comprises selecting the partial region based on the ID device of the operator who logs into a medical diagnostic system, to perform the medical examination of the object.

16. The medical information providing method of claim 1, further comprising obtaining diagnostic information of the object, the diagnostic information comprising at least one among:

an identification (ID) information of the object, information about a diagnostic process with respect to the object, and medical history information of the object.

17. The method of claim 1, wherein the captured room image is a contemporary image of the examination room captured by a camera.

18. The method of claim 1, wherein the displaying further comprises displaying diagnostic information as an overlay on the captured room image.

19. The method of claim 1, wherein the capturing comprises capturing an image of a diagnostic medical apparatus incorporated into the medical information providing apparatus, and the displaying further comprises:
displaying, on a screen of the at least one display, an image of a portion of the diagnostic medical apparatus visually spatially connected to other portion of the diagnostic medical apparatus, the other portion being observable through the console room window, so that the displayed image of the portion of the diagnostic medical apparatus is visually perceived as a continuation of the other portion of the diagnostic medical apparatus.

20. A magnetic resonance imaging (MRI) system or a computed tomography (CT) system which performs the medical information providing method of claim 1.

21. A medical information providing apparatus comprising:
an image capturing device configured to capture a room image of an inside of an examination room in which an object is positioned for medical examination; and
a plurality of displays disposed on a border with a console room window disposed between the examination room and a console room, and configured to display at least a part of the captured room image,
at least one processor configured to:
obtain information of at least one among a position of a user, a distance between the user and each of the plurality of displays, respectively, and a direction of a view of the user,
select, for each of the plurality of displays, a partial region of the captured room image a border of which is matched to a border of a room view observable via the console room window and to an image displayed on at least one display among the plurality of displays, based on the at least one among the position of the user, the distance between the user and each of the plurality of displays, respectively, and the direction of the view of the user, and
control to display the selected partial region of the captured room image, on each of the plurality of displays, respectively.

22. The medical information providing apparatus of claim 21, wherein the at least one processor is further configured to:
define a medical information providing mode to include at least one selected from a first mode configured to provide diagnostic information on the selected partial region of the captured room image, a second mode configured to provide the selected partial region of the captured room image, and a third mode configured to provide the diagnostic information; and
provide at least one selected from the selected partial region of the captured room image and the diagnostic information, according to the medical information providing mode, to the plurality of displays.

23. The medical information providing apparatus of claim 22, wherein the at least one processor is further configured to determine the medical information providing mode for the plurality of displays while a diagnostic process with respect to the object is being performed.

24. The medical information providing apparatus of claim 23, wherein the room image according to the second mode is displayed on the at least one display, prior to beginning of the diagnostic process, the at least one processor is further configured to change the second mode to the third mode or the first mode, in response to the diagnostic process with respect to the object being started, and
the plurality of displays are further configured to display the diagnostic information in the third mode or the first mode, in response to the second mode being changed to the third mode or the first mode.

25. The medical information providing apparatus of claim 22, wherein the at least one processor is further configured to determine the medical information providing mode of the plurality of displays.

26. The medical information providing apparatus of claim 25, wherein the at least one processor is further configured to determine the medical information providing mode of the plurality of displays, respectively, as the third mode or the first mode, in response to a diagnostic process of the object being started.

27. The medical information providing apparatus of claim 25, wherein the at least one processor is further configured to change the medical information providing mode of the plurality of displays, based on priority orders pre-set in the plurality of displays, respectively.

28. The medical information providing apparatus of claim 27, wherein the priority orders are determined based on at least one among a position, a size, and a resolution of the plurality of displays, respectively.

29. The medical information providing apparatus of claim 27, wherein the respective displays comprise a first display and a second display, and
the at least one processor is further configured to provide a first piece of the diagnostic information to the first display in response to a diagnostic process of the object being started, consequently provide the first piece of the diagnostic information to the second display that has a lower priority than that of the first display in response to the diagnostic process of the object being advanced and a second piece of the diagnostic information being obtained, and provide the second piece of the diagnostic information to the first display in response to the second piece of the diagnostic information being obtained.

30. The medical information providing apparatus of claim 25, wherein the plurality of displays is embodied in the console room window, and the plurality of displays is disposed adjacent each other along a side edge of the console room window or on an entirety of the console room window.

31. The medical information providing apparatus of claim 25,
wherein the at least one processor is further configured to select a plurality of partial regions from the room image according to an arrangement of the plurality of displays, match the plurality of partial regions with the plurality of displays, respectively, and provide images of the plurality of partial regions to the plurality of matched displays.

32. The medical information providing apparatus of claim 31, wherein the plurality of partial regions are spatially connected to each other.

33. The medical information providing apparatus of claim 25, further comprising a user input receiver that commonly corresponds to the plurality of displays,
wherein the at least one processor is further configured to control the plurality of displays based on an external input signal received via the user input receiver.

34. The medical information providing apparatus of claim 21, wherein the at least one processor is further configured to select the partial region based on an identification (ID) device configured to identify an operator.

35. The medical information providing apparatus of claim 34, wherein the at least one processor is further configured to select the partial region based on the ID device of the operator who logs into a medical diagnostic system to perform the medical examination of the object.

36. The medical information providing apparatus of claim 21, further comprising a diagnostic information obtainer configured to obtain diagnostic information of the object,
wherein the diagnostic information comprises at least one among:
an identification (ID) information of the object,
information about a diagnostic process with respect to the object, and
medical history information of the object.

37. The medical information providing apparatus of claim 21, further comprising a magnetic resonance imaging (MRI) system or a computed tomography (CT) system.

38. A non-transitory computer-readable recording medium having recorded thereon a program which, when executed by a computer, causes the computer to perform the method of claim 1.

39. An apparatus comprising:
image capturing devices configured to capture a room image including a plurality of partial regions of an inside of a first room, in which an object is positioned for medical imaging;
a room image processor configured to obtain the room image from the image capturing devices and form a visual representation of the room image;
a medical processor configured to process medical imaging information of the object while the medical imaging of the object proceeds and form a medical image of a region of interest (ROI) of the object; and
a plurality of displays which are disposed in an array on a display panel in a second room separated from the first room and configured to display the visual representation of the room image for a larger region than an observed first room inside region via a console room window, by displaying the plurality of partial regions spatially connected to each other, and to display the medical image of the ROI of the object,
wherein the spatially connected plurality of partial regions together display a contagious image of the room image for the larger region than the observed first room inside region, and
wherein at least one display is embodied in the console room window, among the plurality of displays,
wherein the room image processor is further configured to:
obtain information of at least one among a position of a user, a distance between the user and each of the plurality of displays, respectively, and a direction of a view of the user,
select, for each of the plurality of displays, a partial region of the captured room image a border of which is matched to a border of a room view observable via the console room window and to an image displayed on the at least one display, based on the at least one among the position of the user, the distance between the user and each of the plurality of displays, respectively, and the direction of the view of the user, and
display the partial region of the captured room image, on each of the plurality of displays, respectively.

40. The apparatus of claim 36, further comprising:
a user workstation which is disposed in the second room and comprises a user interface (UI) configured to interface with the plurality of displays, and is configured to receive a signal from the user for manipulating one among graphical objects displayed on the UI and physical keys provided with the UI to control plurality of displays.

41. The apparatus of claim 36, wherein the room image processor and the medical processor are embodied in a user workstation.

42. The apparatus comprising of claim 36, further comprising a mode determiner configured to determine a medical information providing mode in the plurality of displays to include at least one among:
a second mode configured to provide the room image,
a third mode configured to provide the medical image, and
a first mode configured to provide the medical image overlaid on the room image.

43. The apparatus comprising of claim 36, wherein the image capturing devices are attached to rear surfaces of corresponding displays.

44. The apparatus comprising of claim 43, wherein the image capturing devices are configured to obtain portions of the room image corresponding to a field of view (FOV) of each of the image capturing devices, respectively,
the room image processor is further configured to provide the portions of the room image to the plurality of displays which have been configured to provide the room image, and
the medical processor is further configured to provide the medical image of the object on at least one among the room image and the plurality of displays configured to provide the medical image.

45. The apparatus comprising of claim 36, wherein the plurality of displays are attached to the display panel side by side to form a seamless display comprising display tiles arranged in an addressable array.

46. An apparatus comprising:
an image capturing device configured to obtain a room image of an inside of a first room, in which an object is positioned for medical imaging;
a medical processor configured to obtain pieces of medical information of the object;
a plurality of displays which are disposed in an array on a display panel in a second room; and
a user workstation which is disposed in the second room, and configured to control the medical imaging of the object and display at least one of the pieces of medical information to be overlaid on the room image for a larger region than an observed first room inside region via a console room window, on the plurality of displays, and
wherein at least one display is embodied in the console room window, among the plurality of displays, and
wherein the user workstation is further configured to:
obtain information of at least one among a position of a user, a distance between the user and each of the plurality of displays, respectively, and a direction of a view of the user,
select, for each of the plurality of displays, a partial region of the captured room image a border of which is matched to a border of a room view observable via the console room window and to an image displayed on the at least one display, based on the at least one among the position of the user, the distance between the user and each of the plurality of displays, respectively, and the direction of the view of the user, and
display the selected partial region of the captured room image, on each of the plurality of displays, respectively.

47. The apparatus of claim 46, wherein the medical processor comprises:
an image processor configured to obtain a medical image of the object and provide the medical image to the plurality of displays;
a pre-processor configured to obtain and provide an imaging schedule of the object to the plurality of displays; and
a contrast monitoring processor configured to control an injection of contrast in the object and provide a contrast monitoring image to the plurality of displays.

48. The apparatus of claim 47, wherein the user workstation is further configured to define an image providing mode and set an image providing order in the plurality of displays, and to control the displaying of the room image, the medical image, the imaging schedule, and the contrast monitoring image based on the image providing mode and the image providing order, on the plurality of displays, respectively.

49. The apparatus of claim 46, further comprising at least one among a computed tomography (CT) imaging system and a magnetic resonance (MR) imaging system,
wherein the user workstation is further configured to provide at least one among a CT image and an MR image to the plurality of displays.

50. The apparatus of claim 49, wherein the medical processor comprises a registration processor configured to superimpose the CT image of a region of interest (ROI) of the object with the MR image of the ROI of the object, and
the user workstation is further configured to provide a superimposed image to the plurality of displays.

* * * * *